US012733949B2

(12) United States Patent
Takikawa

(10) Patent No.: US 12,733,949 B2
(45) Date of Patent: Sep. 15, 2026

(54) FORCEPS DEVICE

(71) Applicant: RIVERFIELD INC., Tokyo (JP)

(72) Inventor: Kyohei Takikawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 0 days.

(21) Appl. No.: 18/773,808

(22) Filed: Jul. 16, 2024

(65) Prior Publication Data

US 2024/0366248 A1 Nov. 7, 2024

Related U.S. Application Data

(63) Continuation of application No. PCT/JP2022/001339, filed on Jan. 17, 2022.

(51) Int. Cl.
*A61B 17/28* (2006.01)
*A61B 34/30* (2016.01)

(52) U.S. Cl.
CPC .......... *A61B 17/2812* (2013.01); *A61B 34/30* (2016.02)

(58) Field of Classification Search
CPC ......... A61B 17/29; A61B 34/71; A61B 34/30; A61B 2017/2903; A61B 2034/305; A61B 17/00234; A61B 17/2909; A61B 2034/302; A61B 2034/715; A61B 2017/2944; A61B 2017/2932; A61B 2017/00327;

(Continued)

(56) References Cited

U.S. PATENT DOCUMENTS

2004/0266574 A1* 12/2004 Jinno .................... A61B 34/71 474/174
2010/0228283 A1* 9/2010 Jinno .................... A61B 34/70 606/205

(Continued)

FOREIGN PATENT DOCUMENTS

CN 107928792 A 4/2018
JP 2004-301275 A 10/2004

(Continued)

OTHER PUBLICATIONS

U.S. Appl. No. 18/773,791, filed Jul. 16, 2024, Kyohei Takikawa.

(Continued)

*Primary Examiner* — Shaun L David
*Assistant Examiner* — Cherie M Poland
(74) *Attorney, Agent, or Firm* — Sughrue Mion, PLLC

(57) ABSTRACT

A forceps device includes grasping portions, a support holding the grasping portions, a first rotating shaft that turnably supports the support, a base member that holds the first rotating shaft, first wires that transmit driving forces to move the grasping portions, first guide pulleys arranged coaxially with the first rotating shaft, the first wires running over the first guide pulleys, respectively, and second guide pulleys arranged upstream of the first guide pulleys, the first wires running over the second guide pulleys, respectively. The second guide pulleys are shifted toward one side relative to a position immediately below the first guide pulleys when the first rotating shaft is viewed in front in an axial direction in a state in which a leading end of the grasping portions points upward, and arranged so that a winding angles γ of the first wires respectively around the first guide pulleys are 65° or larger.

20 Claims, 20 Drawing Sheets

(58) Field of Classification Search
CPC .... A61B 2017/2927; A61B 2017/2947; A61B 2017/00314; A61B 2017/00323; A61B 2017/2908; A61B 2017/292; A61B 2017/2929; A61B 2017/2938; B25J 9/1045
See application file for complete search history.

(56) References Cited

U.S. PATENT DOCUMENTS

2016/0303743 A1 10/2016 Rockrohr
2017/0165017 A1* 6/2017 Chaplin ........... A61B 17/00234
2017/0252096 A1* 9/2017 Felder ................ A61B 18/1445
2018/0311000 A1 11/2018 Ishihara et al.
2019/0099231 A1* 4/2019 Bruehwiler ............ A61B 10/04
2019/0142531 A1* 5/2019 Wentworth ...... A61B 17/00234 606/130
2019/0374297 A1* 12/2019 Wallace ................. A61B 34/30
2020/0093468 A1* 3/2020 Chaplin ................. A61B 34/30
2020/0170728 A1 6/2020 Ishihara et al.
2020/0197112 A1 6/2020 Chin et al.
2020/0246093 A1 8/2020 Sachs et al.
2021/0196416 A1* 7/2021 Betsugi .................. A61B 34/35
2021/0401445 A1 12/2021 Kapadia
2022/0175408 A1 6/2022 Lee et al.
2022/0313296 A1 10/2022 Tadano et al.
2023/0210546 A1* 7/2023 Takikawa ............... A61B 34/30 606/205
2023/0310106 A1* 10/2023 Takikawa ............... A61B 17/29 606/205

FOREIGN PATENT DOCUMENTS

JP 2018-538067 A 12/2018
JP 2020-073013 A 5/2020
JP 6896317 B1 6/2021
JP 6943522 B1 10/2021

OTHER PUBLICATIONS

U.S. Appl. No. 18/773,785, filed Jul. 16, 2024, Kyohei Takikawa.
US Office Action dated Oct. 2, 2025, issued in U.S. Appl. No. 18/773,791.

* cited by examiner

FORCEPS DEVICE

CROSS-REFERENCE TO RELATED APPLICATION

This Application is a Continuation Application of International Application No. PCT/JP2022/001339, filed on Jan. 17, 2022 in the Japan Patent Office, the contents of which being herein incorporated by reference in its entirety.

BACKGROUND

The present disclosure relates to a forceps device used for a manipulator of a surgical robot.

Medical treatments using robots (manipulators) have recently been proposed in order to reduce the burden on operators and save manpower in medical facilities. In the field of surgery, proposals have been made for surgical manipulator systems for operators to treat patients by operating remotely-controllable surgical manipulators.

Various surgical tools may be attached to leading ends of surgical manipulators. Known surgical tools include, for example, forceps for grasping human tissue during surgery.

SUMMARY

It is an aspect to provide a novel technology for improving the durability of wires or improving the controllability of the operation of the forceps device.

According to an aspect of one or more embodiments, there is provided a forceps device comprising a grasping part; a support that holds the grasping part; a first rotating shaft that turnably supports the support; a base member that holds the first rotating shaft; a plurality of grasping-portion wires that transmit driving forces to move the grasping part; a plurality of first guide pulleys arranged coaxially with the first rotating shaft, the plurality of grasping-portion wires running over the plurality of first guide pulleys; and a plurality of second guide pulleys arranged upstream of the plurality of first guide pulleys, the plurality of grasping-portion wires running over the plurality of second guide pulleys. The plurality of second guide pulleys are shifted toward one side relative to a position immediately below the plurality of first guide pulleys when the first rotating shaft is viewed in front in an axial direction in a state in which a leading end of the grasping part points upward; and arranged so that a plurality of winding angles γ of the plurality of grasping-portion wires around the plurality of first guide pulleys are 65° or larger at a neutral position at which the support is not turned to left or right.

According to another aspect of one or more embodiments, there is provided a forceps device comprising a plurality of grasping portions; a support that holds the plurality of grasping portions; a first rotating shaft that turnably supports the support; a base member that holds the first rotating shaft; a plurality of first wires that transmit driving forces to move the plurality of grasping portions; a plurality of first guide pulleys arranged coaxially with the first rotating shaft, the plurality of first wires running over the plurality of first guide pulleys, respectively; and a plurality of second guide pulleys arranged upstream of the plurality of first guide pulleys, the plurality of first wires running over the plurality of second guide pulleys, respectively. The plurality of second guide pulleys are shifted toward one side relative to a position immediately below the plurality of first guide pulleys when the first rotating shaft is viewed in front in an axial direction in a state in which a leading end of the plurality of grasping portions points upward; and arranged so that a plurality of winding angles γ of the plurality of first wires respective around the plurality of first guide pulleys are 65° or larger at a neutral position at which the support is not turned to left or right.

BRIEF DESCRIPTION OF DRAWINGS

The above and other aspects will be described more fully below with reference to the drawings, in which.

DETAILED DESCRIPTION OF EMBODIMENTS

Figure 1:
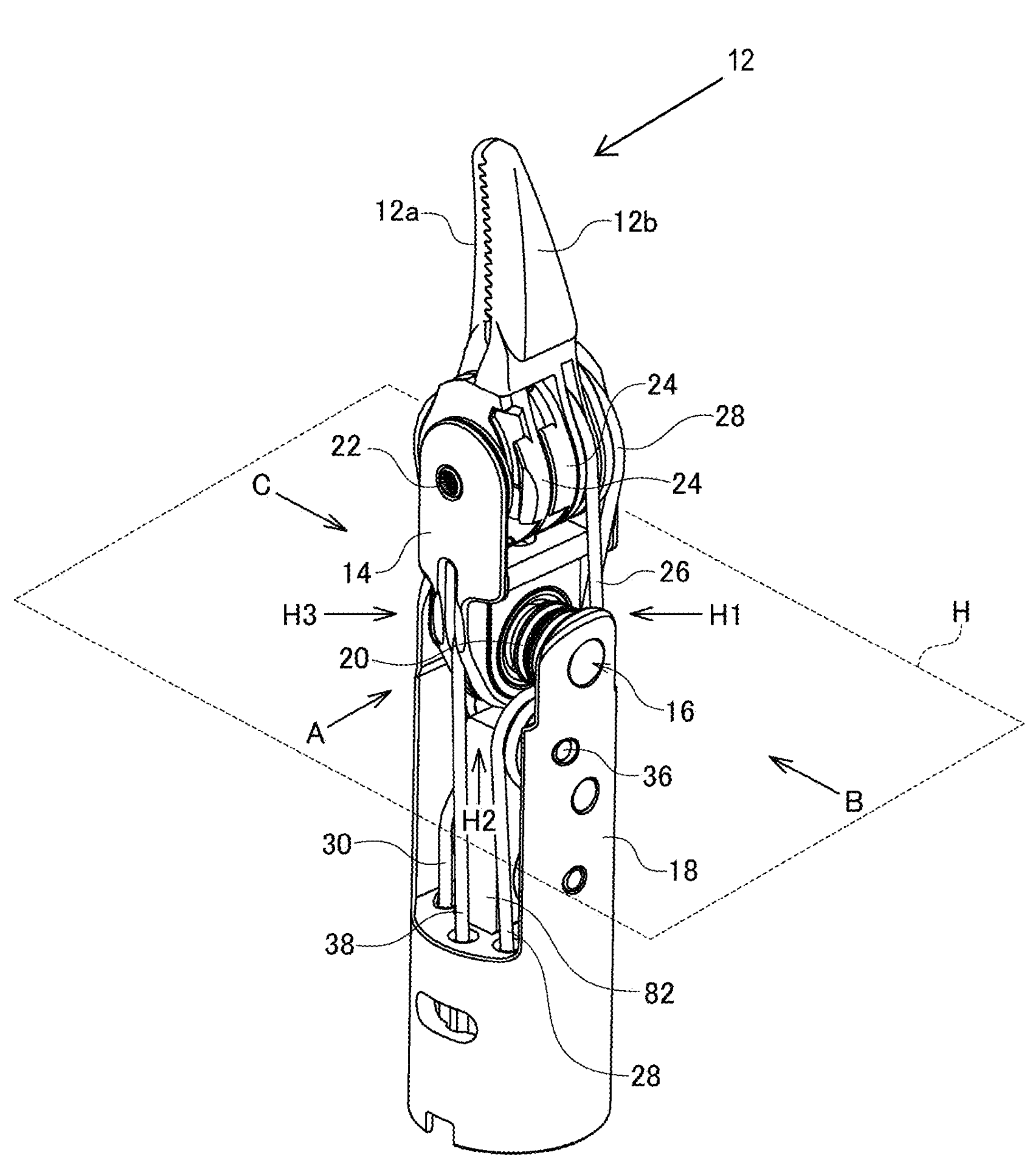
FIG. 1 is a perspective view of a forceps device according to an embodiment.

In the related art, a forceps device may include a first rotating shaft that turnably supports a support holding a grasping part, a base member that holds the first rotating shaft, a plurality of first guide pulleys arranged coaxially with the first rotating shaft, a plurality of grasping-portion wires that transmit driving forces to move the grasping part, the grasping-portion wires running between the plurality of first guide pulleys and the grasping part without other pulleys, and a second rotating shaft that turnably supports second guide pulleys located upstream of the first guide pulleys.

In the related art forceps device mentioned above, there are several disadvantages. For example, in the related art forceps device, the first guide pulleys and the second guide pulleys arranged in parallel with the central axis of the support. Thus, in order to wind the grasping-portion wires around the first guide pulleys, which are coaxial with the first rotating shaft, in accordance with the range of movement of the grasping part, the first guide pulleys and the second guide pulleys need to be close to each other. If the first guide pulleys and the second guide pulleys are close to each other, however, the radii of curvature of the wound grasping-portion wires are small. When the grasping-portion wires in this state are repeatedly pulled, the durability of the grasping-portion wires may significantly lower. Furthermore, if the tensions of the grasping-portion wires are increased so as to increase the grasping force of the grasping part of the aforementioned forceps device, the frictional force between the first rotating shaft and the support increases, which lowers the controllability of the bending movement of the support including the grasping part about the first rotating shaft.

It is an aspect to provide a novel technology for improving the durability of wires or improving the controllability of the operation of the forceps device.

To address the aforementioned disadvantages, a forceps device according to an embodiment may include a grasping part; a support that holds the grasping part; a first rotating shaft that turnably supports the support; a base member that holds the first rotating shaft; a plurality of grasping-portion wires that transmit driving forces to move the grasping part; first guide pulleys arranged coaxially with the first rotating shaft, the grasping-portion wires running over the first guide pulleys; and second guide pulleys arranged upstream of the first guide pulleys, the grasping-portion wires running over the second guide pulleys. The second guide pulleys are: (i) shifted toward one side relative to immediately below the first guide pulleys when the first rotating shaft is viewed in front in an axial direction in a state in which a leading end of a grasping part points upward; and (ii) arranged so that winding angles γ of the grasping-portion wires around the first guide pulleys are 65° or larger at a neutral position at which the support is not turned to left or right.

According to this aspect, comfortable operation control can be achieved with the turning angle of the support, which holds the grasping part, being at least within a range of ±65°.

In some embodiments, the winding angles γ may be 89° or larger. This confirmation enables comfortable operation control with the turning angle of the support, which holds the grasping part, being at least within a range of ±89°.

In some embodiments, the forceps device may further include third guide pulleys arranged upstream of the second guide pulleys, the grasping-portion wires running over the third guide pulleys. The third guide pulleys may be: (i) shifted toward one side relative to immediately below the first guide pulleys when the first rotating shaft is viewed in front in the axial direction in the state in which the leading end of the grasping part points upward; and (ii) shifted toward the other side relative to immediately below the second guide pulleys when the first rotating shaft is viewed in front in the axial direction in the state in which the leading end of the grasping part points upward. This configuration increases the radius of curvature of an S-shaped curve of the grasping-portion wires running over the second guide pulleys and the third guide pulleys. Furthermore, as a result of the increase in the radius of curvature of the S-shaped curve of the grasping-portion wires, bending stress generated in the grasping-portion wires is lowered, and the durability of the grasping-portion wires relating to opening and closing movements of the grasping part is improved.

In some embodiments, the third guide pulleys may be a pair of guide pulleys arranged on respective sides of an inner wall of the base member, and the pair of third guide pulleys may be rotatably supported by different support shafts, respectively, held by the base member. This configuration enables the third guide pulleys and the second guide pulleys to be arranged on the same side (right side or left side) when the first guide pulleys are viewed from the front.

In some embodiments, the base member may be a cylindrical part having an outer diameter of 7 to 9 mm, the first guide pulleys may have a diameter of 3.0 to 3.6 mm, the second guide pulleys may have a diameter of 3.0 to 3.6 mm, and the third guide pulleys may have a diameter of 3.0 to 3.6 mm. As a result, in a forceps device having a very small outer diameter, the radius of curvature of each S-shaped curve can be increased while appropriate winding angles are achieved.

A method, a device, a system, and the like consistent with the above description of various embodiments may also be provided to address the above-described disadvantages over the related art.

According to the various embodiments, the durability of wires or the controllability of the operation of the forceps device is improved.

Various embodiments will now be described with reference to the drawings. Components, members, and processes that are the same as or equivalent to each other illustrated in the drawings are represented by the same reference numerals, and redundant explanation will not be repeated for conciseness. The various embodiments are not limited to those described herein, but rather are examples, and in the various embodiments, it is to be understood that any feature or any combination of features described are not necessarily essential to the invention.

[Forceps Device]

Figure 2:
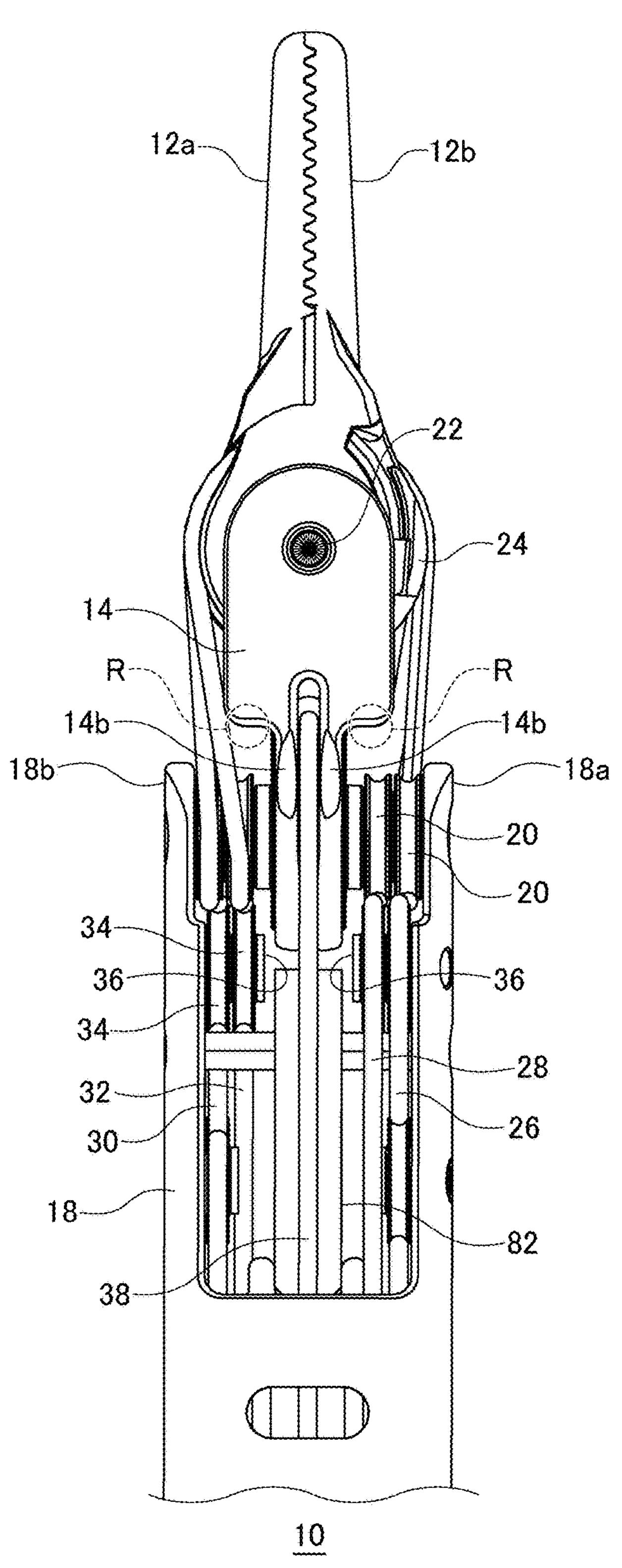
FIG. 2 is a front view of the forceps device of FIG. 1 as viewed in a direction A.
Figure 3:
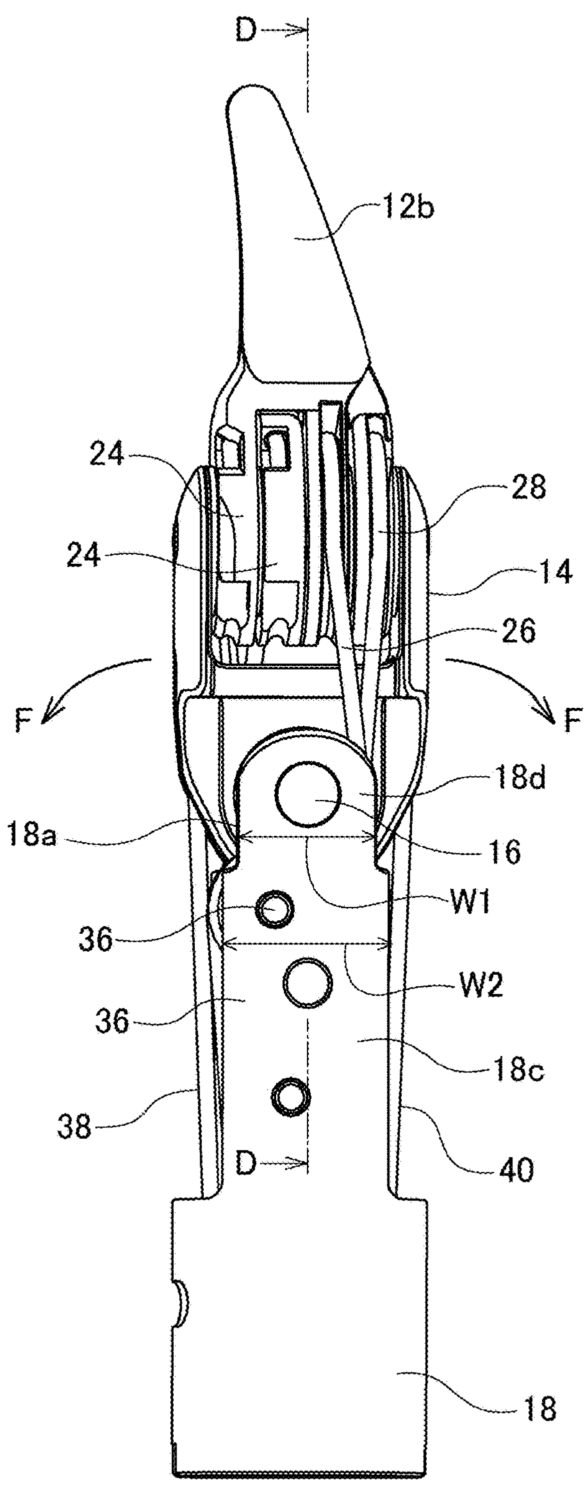
FIG. 3 is a side view of the forceps device of FIG. 1 as viewed in a direction B.
Figure 4:
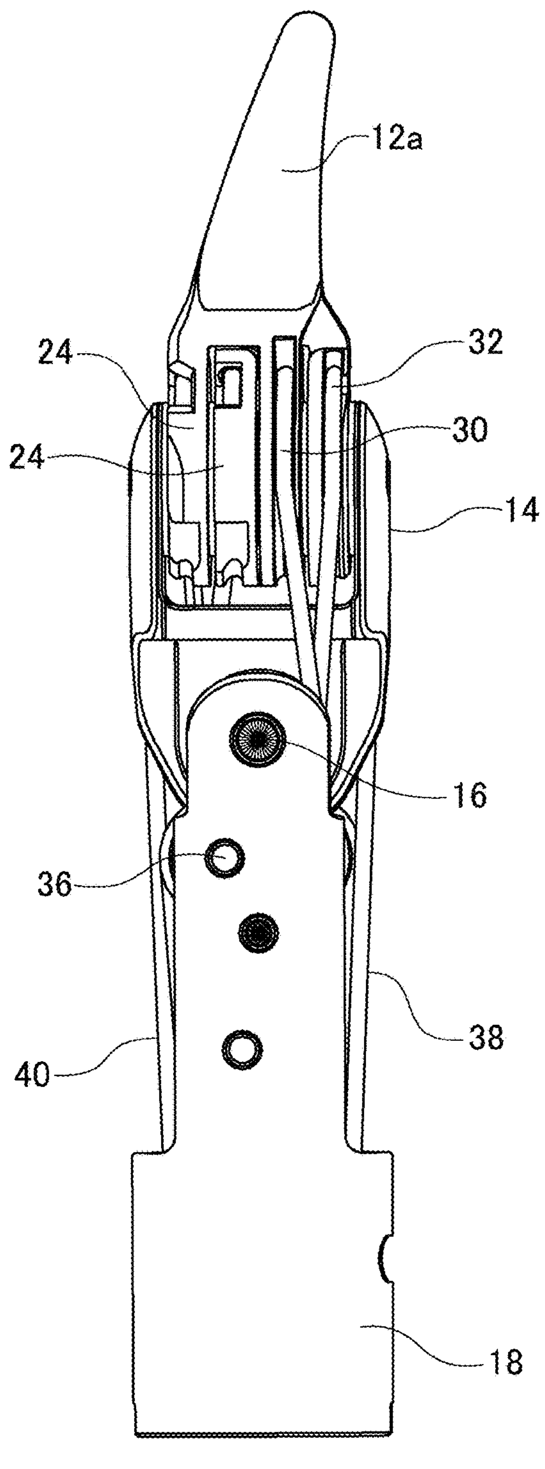
FIG. 4 is a side view of the forceps device of FIG. 1 as viewed in a direction C.

FIG. 1 is a perspective view of a forceps device according to an embodiment. FIG. 2 is a front view of the forceps device of FIG. 1 as viewed in a direction A. FIG. 3 is a side view of the forceps device of FIG. 1 as viewed in a direction B. FIG. 4 is a side view of the forceps device of FIG. 1 as viewed in a direction C.

The forceps device 10 illustrated in the drawings includes a pair of grasping portions 12*a* and 12*b* (collectively a grasping part 12), a support 14 that holds the pair of grasping portions 12*a* and 12*b*, a first rotating shaft 16 that turnably supports the support 14, a base member 18 that holds the first rotating shaft 16, four guide pulleys 20 arranged coaxially with the first rotating shaft 16, a second rotating shaft 22 that turnably supports the pair of grasping portions 12*a* and 12*b* and is held by the support 14, four jaw pulleys 24 supported coaxially with the second rotating shaft 22, four wires 26, 28, 30 and 32 running over the four guide pulleys 20 and the four jaw pulleys 24, and support wires 38 and 40 for turning the support 14 about the first rotating shaft 16.

[Guide Pulleys 20]

Figure 5:
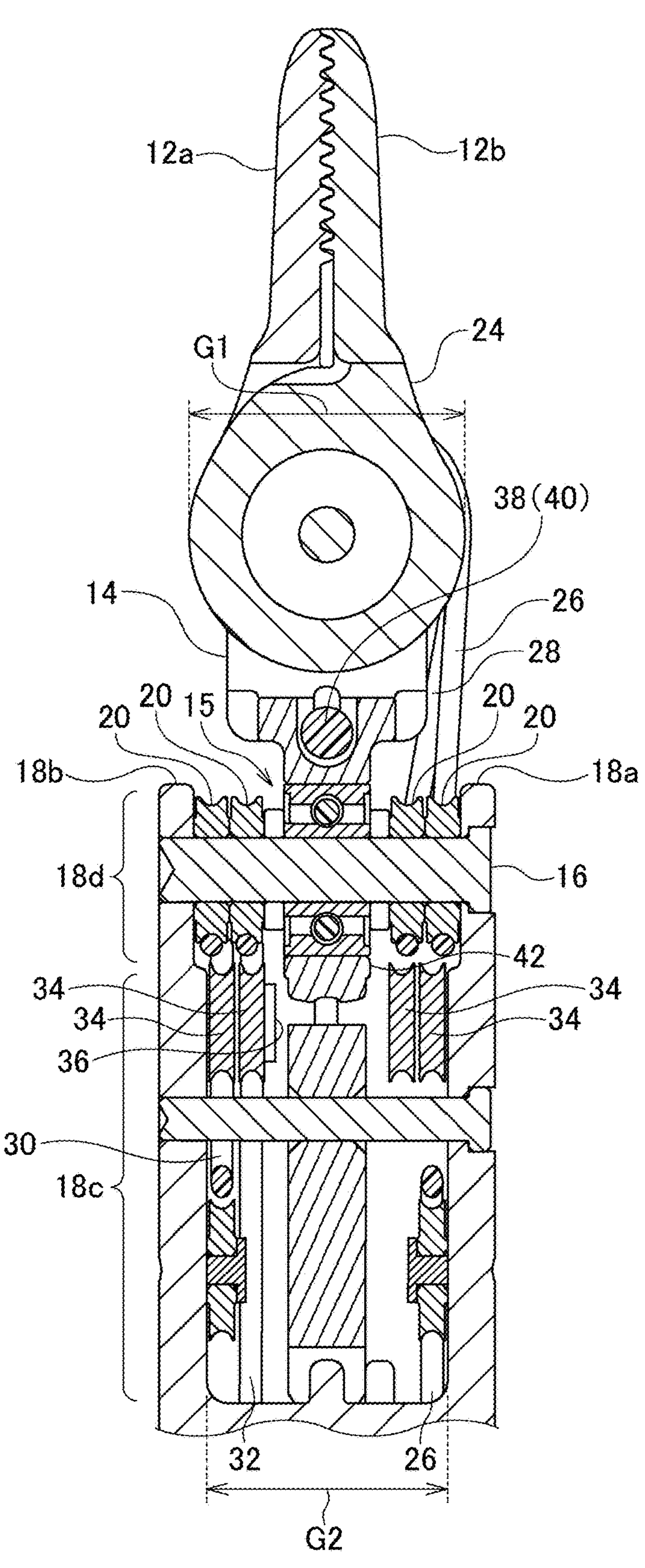
FIG. 5 is a cross-sectional view of the forceps device illustrated in FIG. 3 along D-D.

FIG. 5 is a cross-sectional view of the forceps device 10 illustrated in FIG. 3 along D-D. As illustrated in FIG. 5, the guide pulleys 20 are rotatably supported by the first rotating shaft 16 inserted in a bearing 15 mounted on the support 14. As illustrated in FIG. 5, the guide pulleys 20 are arranged in such a manner that two guide pulleys 20 adjacent to each other are present on respective sides with respect to the support 14.

[Base Member]

Next, the base member 18 will be described. As illustrated in FIG. 2 and FIG. 5, the base member 18 includes a pair of arms 18*a* and 18*b* that hold respective ends of the first rotating shaft 16, and third rotating shafts 36 that are held by the pair of arms 18*a* and 18*b*, respectively, and rotatably support four guide pulleys 34 located upstream of the guide pulleys 20. Note that a third rotating shaft 36 is provided on each of the pair of arms 18*a* and 18*b*. In some embodiments, the two rotating shafts 36 are arranged with their axial directions being parallel to each other but not being aligned with each other.

The arms 18*a* and 18*b* each have a base part 18*c* holding the third rotating shaft 36, and a distal end part 18*d* that holds the first rotating shaft 16 and that is thinner than the base part 18*c*. In other words, the distance between the distal end parts 18*d* is larger than the distance between the base parts 18*c*. Thus, as illustrated in FIG. 3, even when the wires 26 and 28 having the fleet angles are bent together with the support 14 around the first rotating shaft 16 (in the direction of an arrow F in FIG. 3), the wires 26 and 28 are less likely to interfere with the arms 18*a* and 18*b*.

Furthermore, the circumferential width W1 of the distal end part 18*d* of the arm 18*a* (the arm 18*b*) is smaller than the circumferential width W2 of the base part 18*c* thereof. Thus, a U-shaped recess is formed at the distal end part 18*d* at which interference with a wire may be addressed, and the circumferential width of the distal end part 18*d* is made larger than the circumferential width of the base part 18*c*, which minimizes deterioration of the stiffness of the arm.

In some embodiments, as illustrated in FIG. 5, the jaw pulleys 24 have an outer diameter G1, which is larger than the distance between the base parts 18*c* of the pair of arms 18*a* and 18*b*. Thus, in the forceps device 10, the jaw pulleys 24 having a large outer diameter relative to the inner diameter of the cylindrical base member 18 may be used.

[Support]

Figure 6:
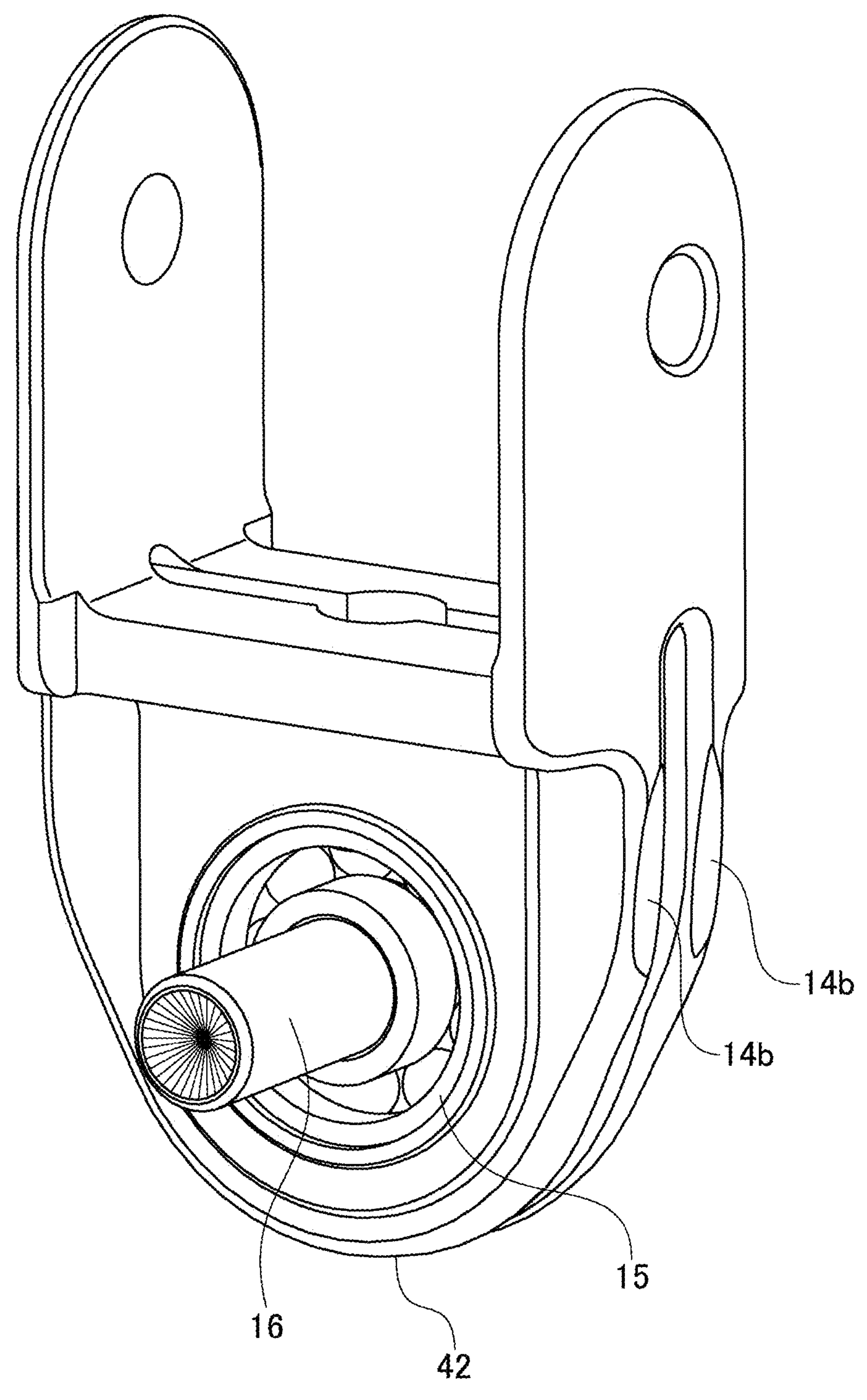
FIG. 6 is a perspective view of a support according to an embodiment.
Figure 7:
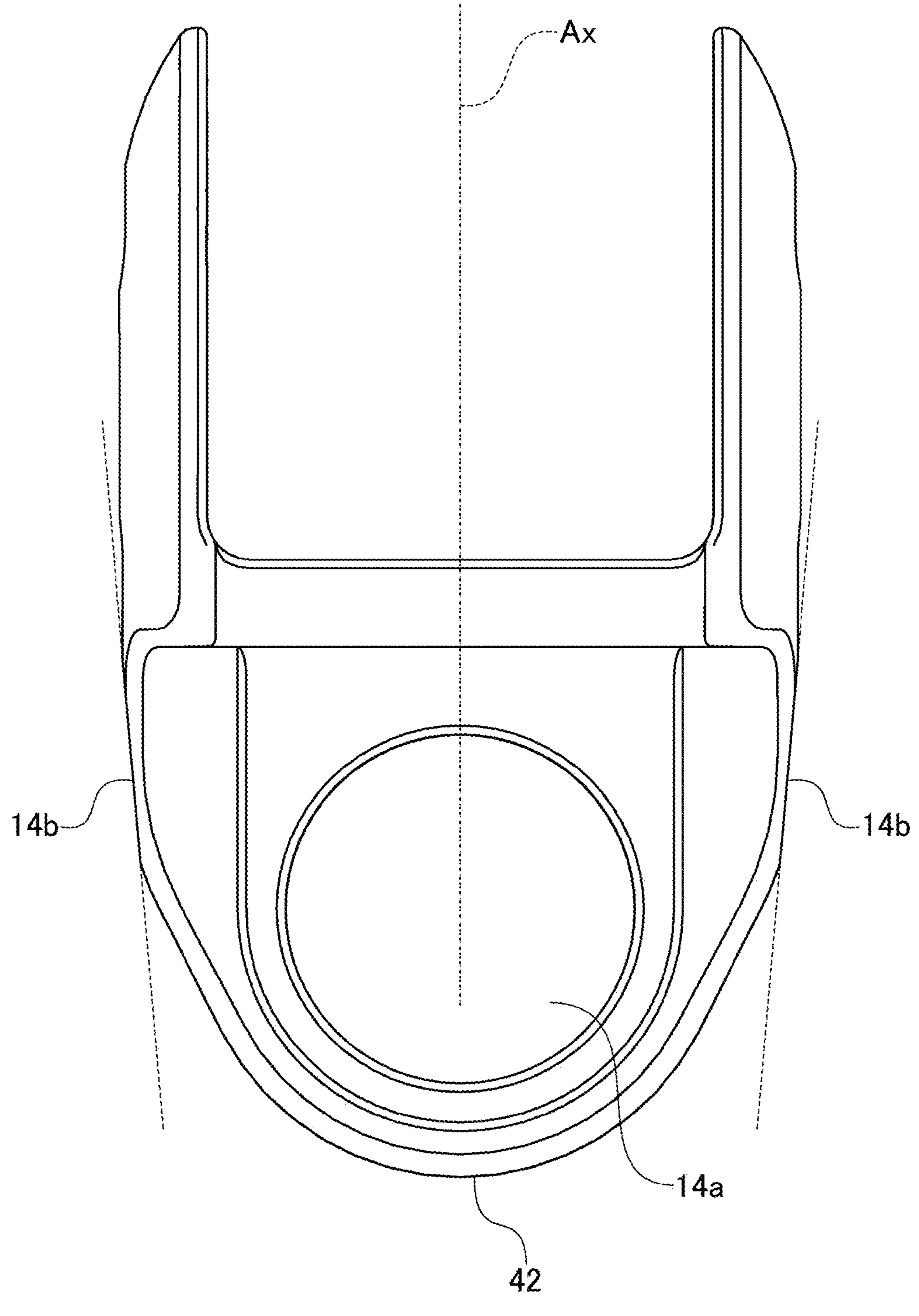
FIG. 7 is a front view of the support according to an embodiment.
Figure 8:
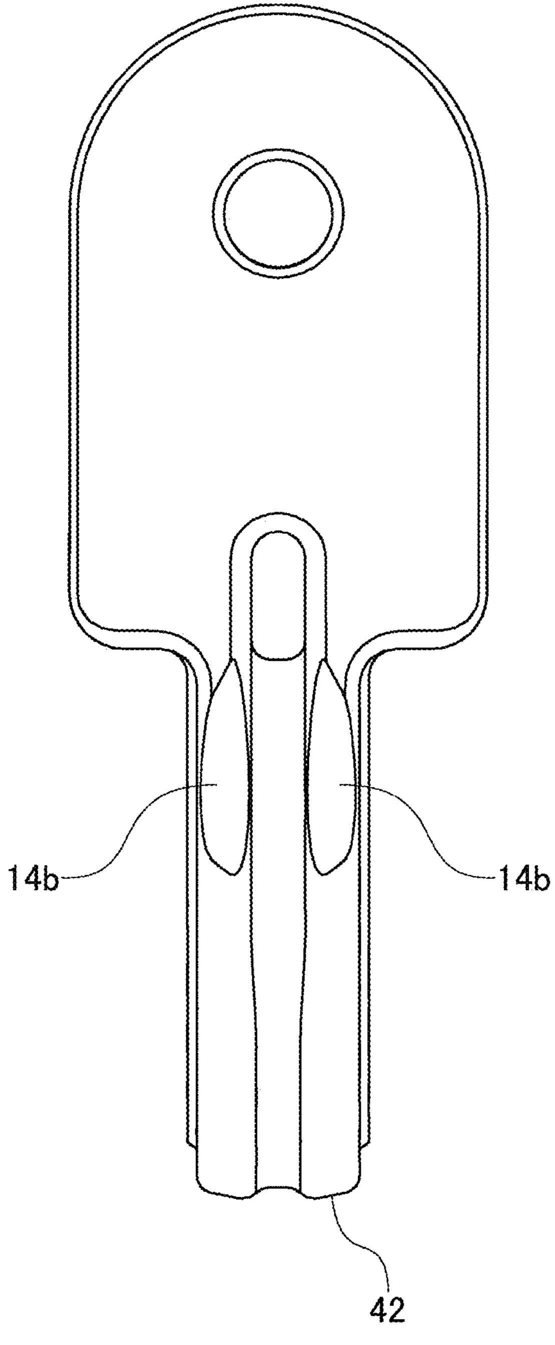
FIG. 8 is a side view of the support according to an embodiment.

FIG. 6 is a perspective view of a support according to an embodiment. FIG. 7 is a front view of the support. FIG. 8 is a side view of the support. As illustrated in FIG. 5, the forceps device 10 includes the pair of grasping portions 12*a* and 12*b*, the support 14 that holds the pair of grasping portions 12*a* and 12*b*, the first rotating shaft 16 that turnably supports the support 14, the base member 18 that holds the first rotating shaft 16, and a plurality of guide pulleys 20 arranged coaxially with the first rotating shaft 16.

As illustrated in FIG. 7, the support 14 has a circular through-hole 14*a* in which the bearing 15, which is a shaft bearing, is mounted. In some embodiments, as illustrated in FIG. 6, the first rotating shaft 16, which rotatably supports the support 14, is inserted into the bearing 15 mounted on the support 14. The guide pulleys 20 are rotatably supported by the outer circumference of the first rotating shaft 16. Note that each rotating shaft is not limited to a shaft that rotates by itself, but may be any shaft that is the center of rotation of a member supported thereby, and may be a shaft fixed to another member.

In the forceps device 10 having such a structure, the support 14 in a state in which a plurality of guide pulleys 20 are supported by the outer circumference of the first rotating shaft 16 is held by the base member 18 with the first rotating shaft 16 therebetween. This configuration facilitates improvement in the easiness of assembly as compared with a case where the support 14 is held directly by the base member 18.

In some embodiments, the base member 18 has the pair of arms 18*a* and 18*b* facing each other. The first rotating shaft 16 is firmly fixed in such a manner that the axial ends thereof are press-fitted to the pair of arms 18*a* and 18*b*. As a result, because the distal ends of the pair of arms 18*a* and 18*b*, which can be free ends, are fixed by the rotating shaft, the stiffness of the whole base member 18 increases.

Each of the wires 26, 28, 30 and 32 transmits a driving force to the grasping portion 12*a* or the grasping portion 12*b* to move the grasping portion 12*a* or the grasping portion 12*b*. Specifically, the wire 26 and the wire 32 run over the jaw pulleys 24 for the grasping portion 12*b*, and the grasping portion 12*b* moves in an opening direction when the wire 26 is pulled and moves in a closing direction when the wire 32 is pulled. The wire 28 and the wire 30 run over the jaw pulleys 24 for the grasping portion 12*a*, and the grasping portion 12*a* moves in a closing direction when the wire 28 is pulled and moves in an opening direction when the wire 30 is pulled.

In some embodiments, each of the four guide pulleys 20 has a corresponding one of the wires 26, 28, 30 and 32 placed thereover. As illustrated in FIG. 2, each of the wires 26, 28, 30 and 32 passes between the corresponding ones of the guide pulleys 20 and guide pulleys 34 and runs over the corresponding one of the guide pulleys 20 from a lower side thereof (a side opposite the grasping portion 12*a* or 12*b* with respect to the first rotating shaft 16).

A support pulley 42, over which the wires 38 and 40 for transmitting a driving force for turning the support about the first rotating shaft 16 run, is formed integrally with part of the support 14. The support pulley 42 is arranged coaxially with the first rotating shaft 16. Thus, when one of the wires 38 and 40 is pulled to turn the support 14, the tension of the wire 38 or 40 running over the support pulley 42 presses the support 14 toward the first rotating shaft 16. A normal force received by the support 14 from the first rotating shaft 16 is thus generated, which contributes to an increase in frictional force. In some embodiments, when one of the wires 26, 28, 30, and 32 is pulled to turn the grasping portions 12*a* and 12*b*, the tension of the wires 26, 28, 30, and 32 is applied to the second rotating shaft 22 via the jaw pulleys 24. The force applied to the inner circumference of the through-hole of the support 14 for supporting the second rotating shaft 22 is then transmitted to the circular through-hole 14*a* in which the bearing 15 is mounted, and the support 14 is thus pressed toward the first rotating shaft 16. In this case as well, a normal force received by the support 14 from the first rotating shaft 16 is generated, which contributes to an increase in frictional force.

In the forceps device 10, however, the bearing is provided between the support 14 and the first rotating shaft 16, which reduces the frictional force between the first rotating shaft 16 and the support 14. Note that, when the bearing 15 is a rolling bearing, the frictional force between the first rotating shaft 16 and the support 14 can further be reduced. Consequently, the movement of the grasping portions 12*a* and 12*b* becomes smoother, and the controllability of the forceps device 10 improves. Note that the bearing may be a plain bearing. The bearing 15 may have a diameter of 3.6 to 4.5 mm, and the guide pulleys 20 may have a diameter of 3.0 to 3.6 mm. The bearing 15 may have a diameter larger than that of the guide pulleys 20.

[Grasping Portions]

Figure 9:
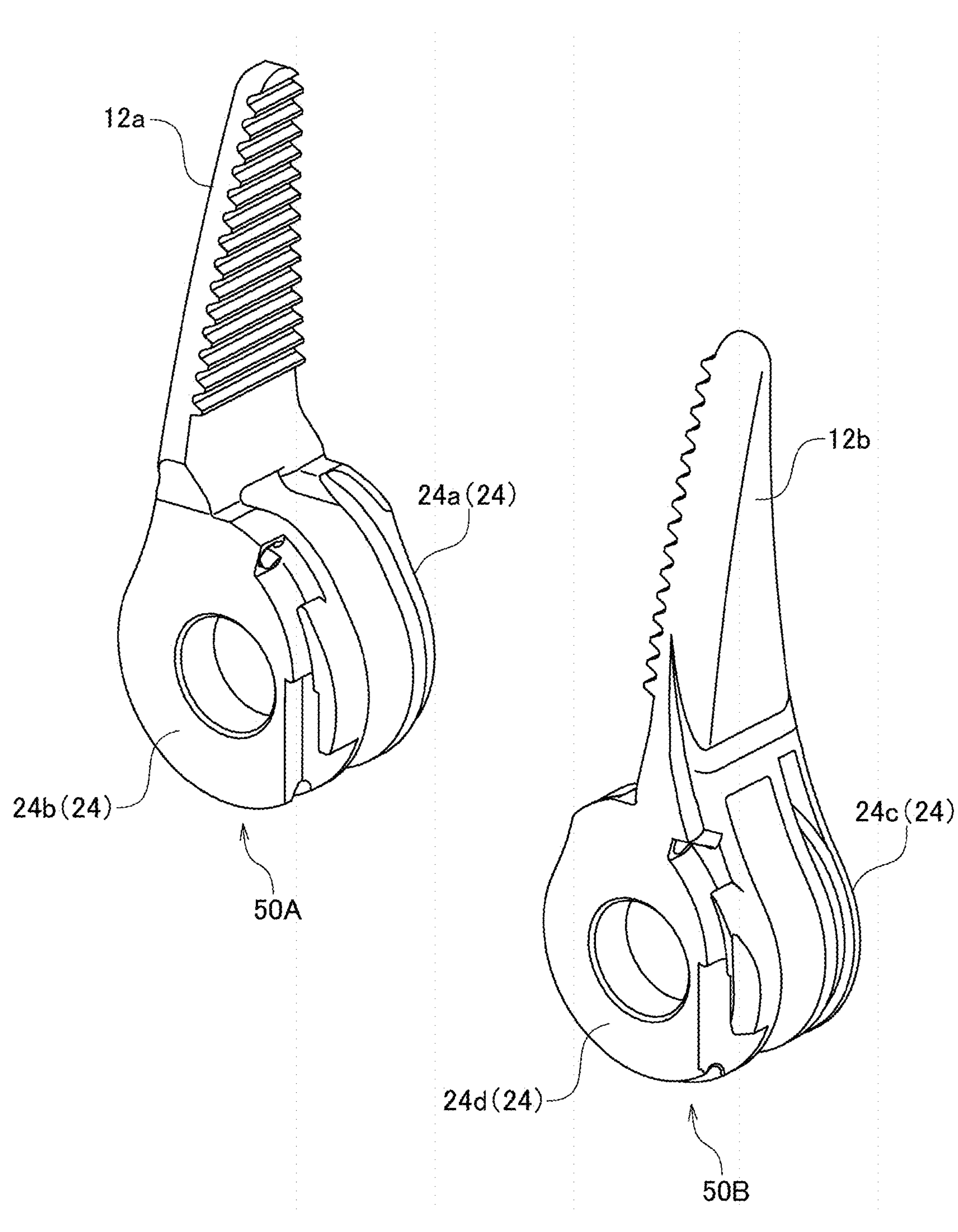
FIG. 9 is a perspective view illustrating a state in which a pair of jaw parts facing each other are to be fitted according to an embodiment.

Next, jaw parts constituting the grasping portions will be described in detail. FIG. 9 is a perspective view illustrating a state in which a pair of jaw parts facing each other are to be fitted. Jaw parts 50A and 50B illustrated in FIG. 9 are parts having substantially the same shapes as each other. The jaw parts 50A and 50B have the grasping portion 12*a* and the grasping portion 12*b*, respectively, which move relative to each other to grasp an object. The grasping portion 12*a* is continuous with a jaw pulley 24*a* (first grasping portion pulley) and a jaw pulley 24*b* (second grasping portion pulley), which are formed in a bifurcated shape, and the grasping portion 12*a* and the jaw pulleys 24*a* and 24*b* integrally constitute the jaw part 50A. In some embodiments, the grasping portion 12*b* is continuous with a jaw pulley 24*c* (third grasping portion pulley) and a jaw pulley 24*d* (fourth grasping portion pulley), which are formed in a bifurcated shape, and the grasping portion 12*b* and the jaw pulleys 24*c* and 24*d* integrally constitute the jaw part 50B.

Figure 10:
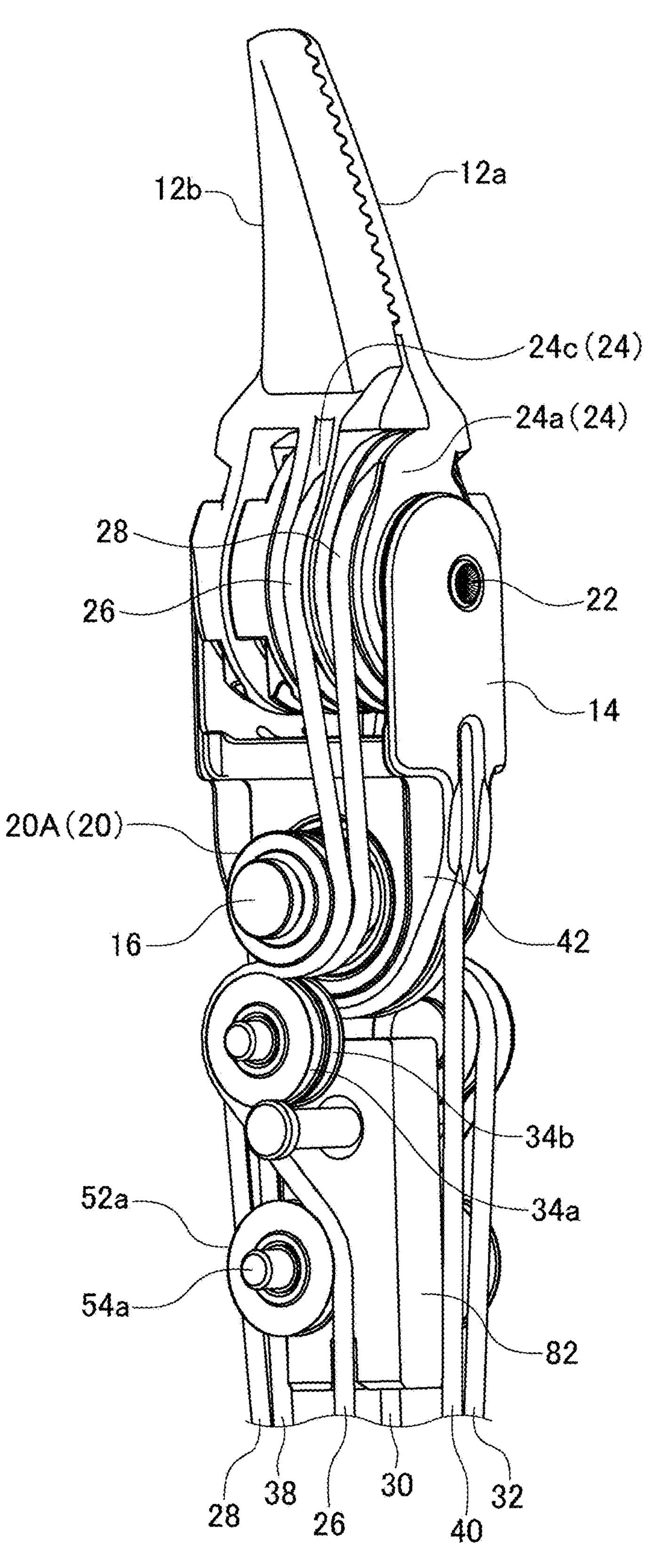
FIG. 10 is a perspective view of the forceps device illustrated in FIG. 1 as viewed in a direction H1.
Figure 11:
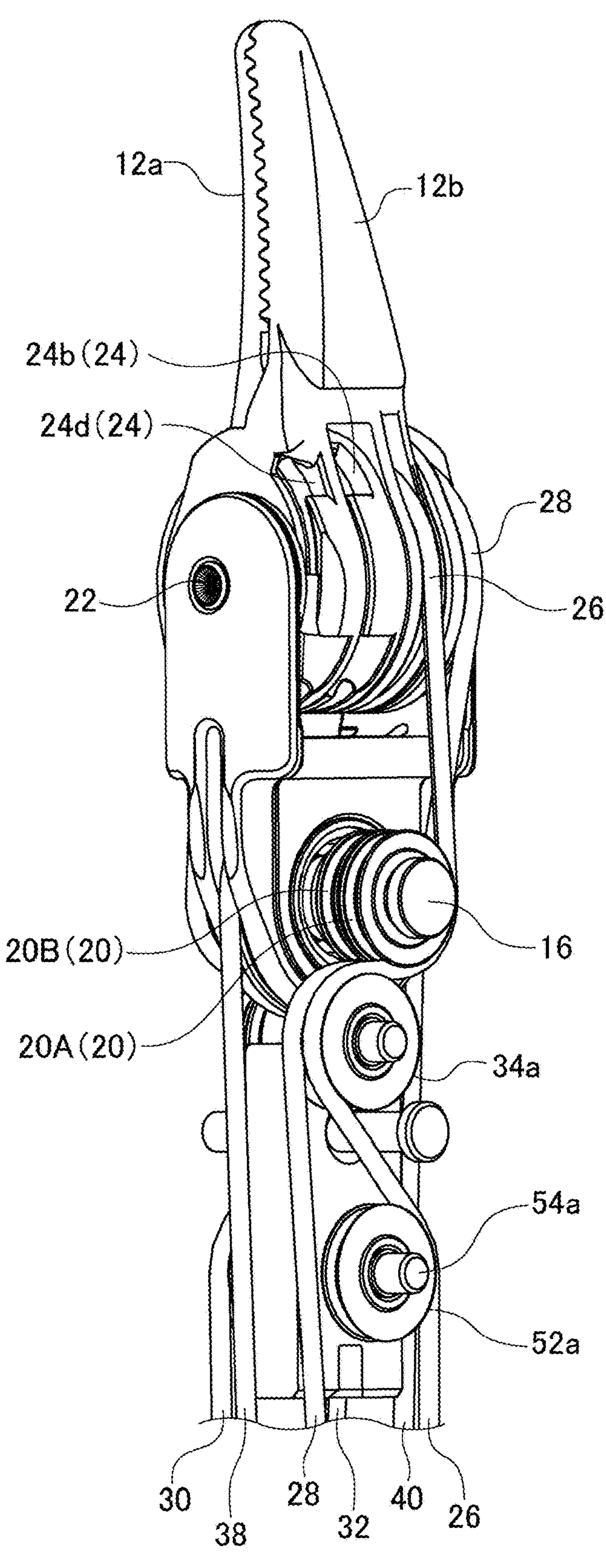
FIG. 11 is a perspective view of the forceps device illustrated in FIG. 1 as viewed in a direction H2.
Figure 12:
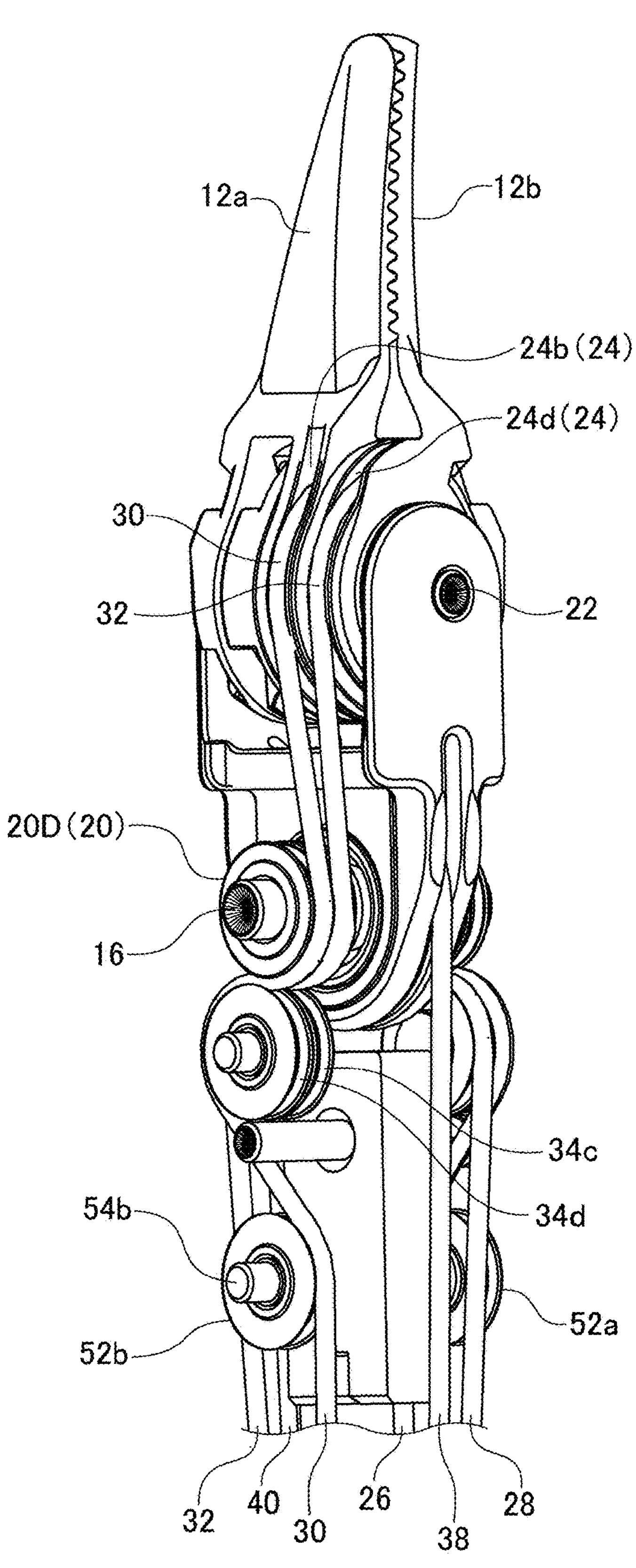
FIG. 12 is a perspective view of the forceps device illustrated in FIG. 1 as viewed in a direction H3.
Figure 13:
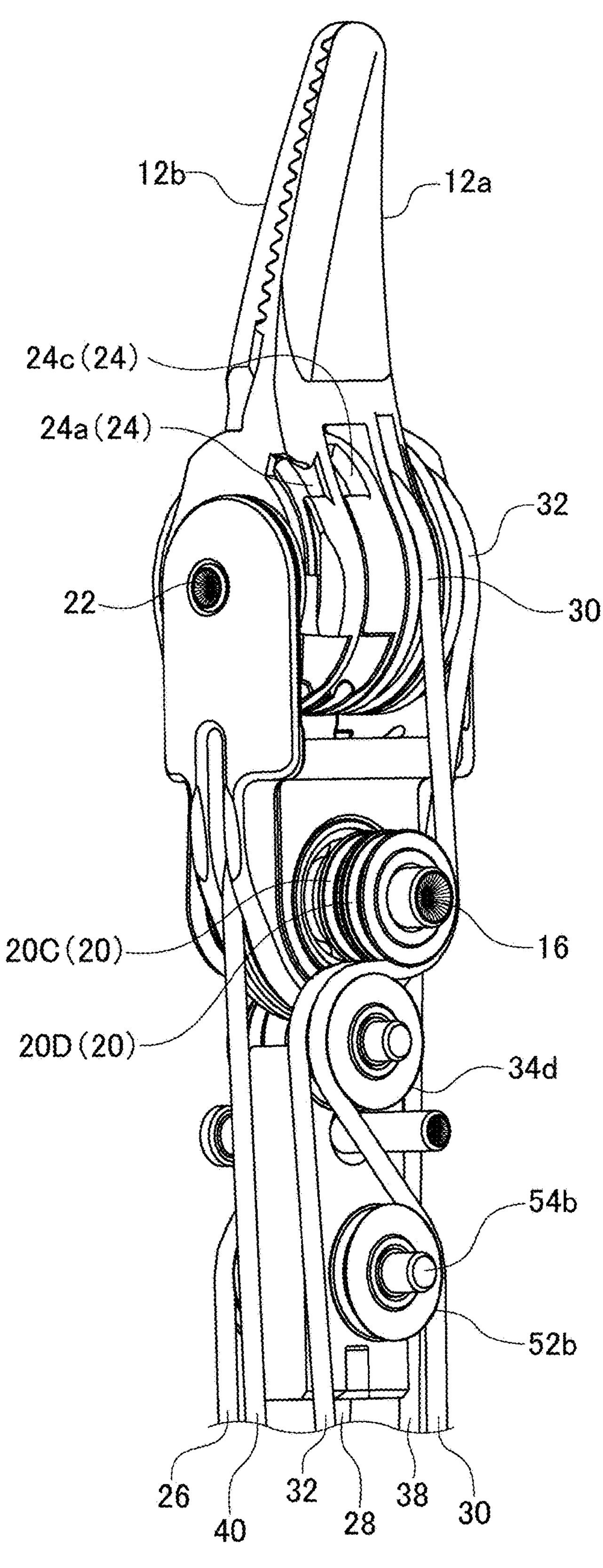
FIG. 13 is a perspective view of the forceps device illustrated in FIG. 1 as viewed in a direction opposite the direction H2.

FIG. 10 is a perspective view of the forceps device 10 illustrated in FIG. 1 as viewed in a direction H1. FIG. 11 is a perspective view of the forceps device 10 illustrated in FIG. 1 as viewed in a direction H2. FIG. 12 is a perspective view of the forceps device 10 illustrated in FIG. 1 as viewed in a direction H3. FIG. 13 is a perspective view of the forceps device 10 illustrated in FIG. 1 as viewed in a direction opposite the direction H2. Note that the directions H1 to H3 are directions within a horizontal plane H including the first rotating shaft 16. It is noted that the base member 18 is not illustrated in FIGS. 10 to 13.

As illustrated in FIGS. 10 to 13, the jaw pulley 24*a*, the jaw pulley 24*c*, the jaw pulley 24*b*, and the jaw pulley 24*d* are rotatably supported in this order by the second rotating shaft 22. In some embodiments, the guide pulley 20A, the guide pulley 20B, the guide pulley 20C, and the guide pulley 20D are rotatably supported in this order by the first rotating shaft 16. The wires 26, 28, 30 and 32, which are grasping-portion wires for transmitting driving forces for causing the grasping portions 12*a* and 12*b* to perform opening and closing movements, run between the guide pulleys 20A to 20D and the grasping portions 12*a* and 12*b* without other pulleys. Note that the driving forces are input from an actuator unit outside of the forceps device 10. This configuration can shorten the distance between the first rotating shaft 16 and the second rotating shaft 22 as illustrated in FIG. 10, etc., and can therefore increase the torque (operation force) of the grasping portions 12*a* and 12*b*. Consequently, the forceps device 10 with high controllability of the grasping portions 12*a* and 12*b* can be provided.

[How Wires Run Over Pulleys]

Next, the manner in which the wires 26, 28, 30 and 32 run over the pulleys will be described in detail. The wire 26 runs between the guide pulley 20A and the jaw pulley 24*c*. The wire 28 runs between the guide pulley 20B and the jaw pulley 24*a*. The wire 30 runs between the guide pulley 20D and the jaw pulley 24*b*. The wire 32 runs between the guide pulley 20C and the jaw pulley 24*d*.

Figure 14:
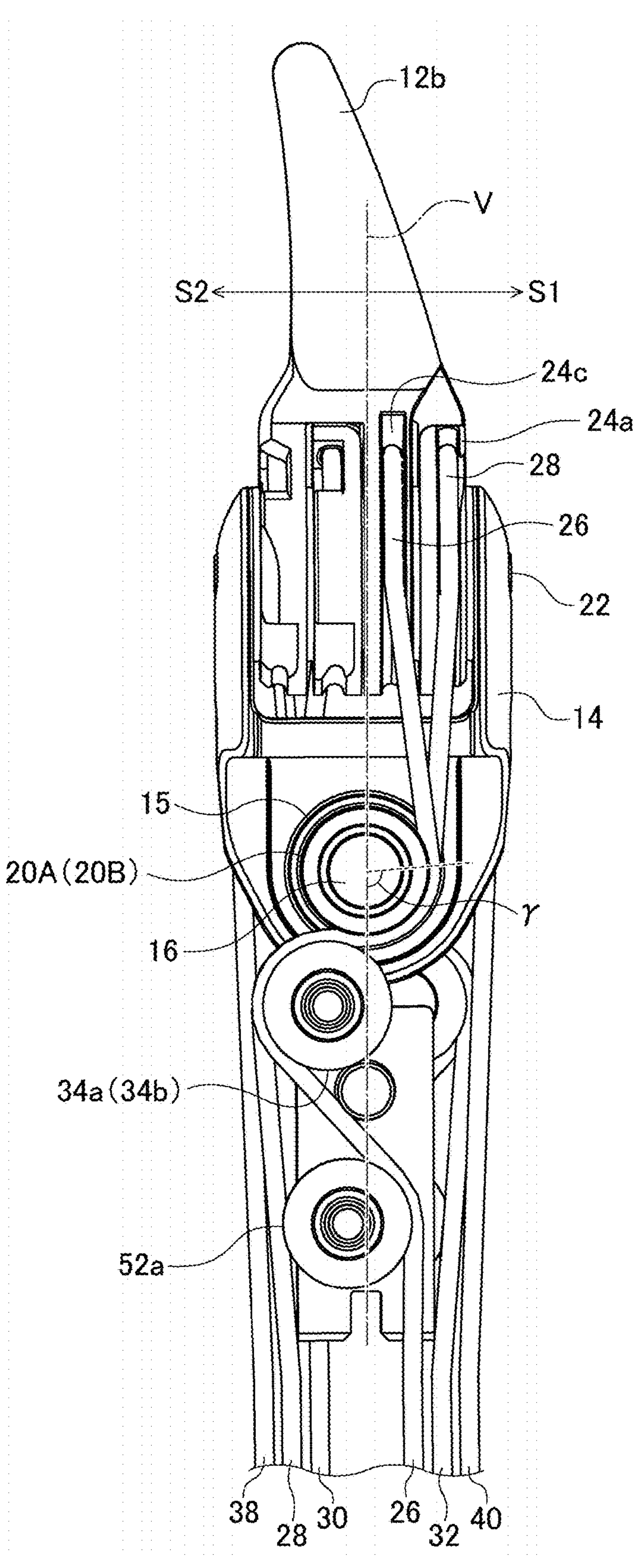
FIG. 14 is a schematic view of the forceps device illustrated in FIG. 3 omitting a base member, according to some embodiments.
Figure 15:
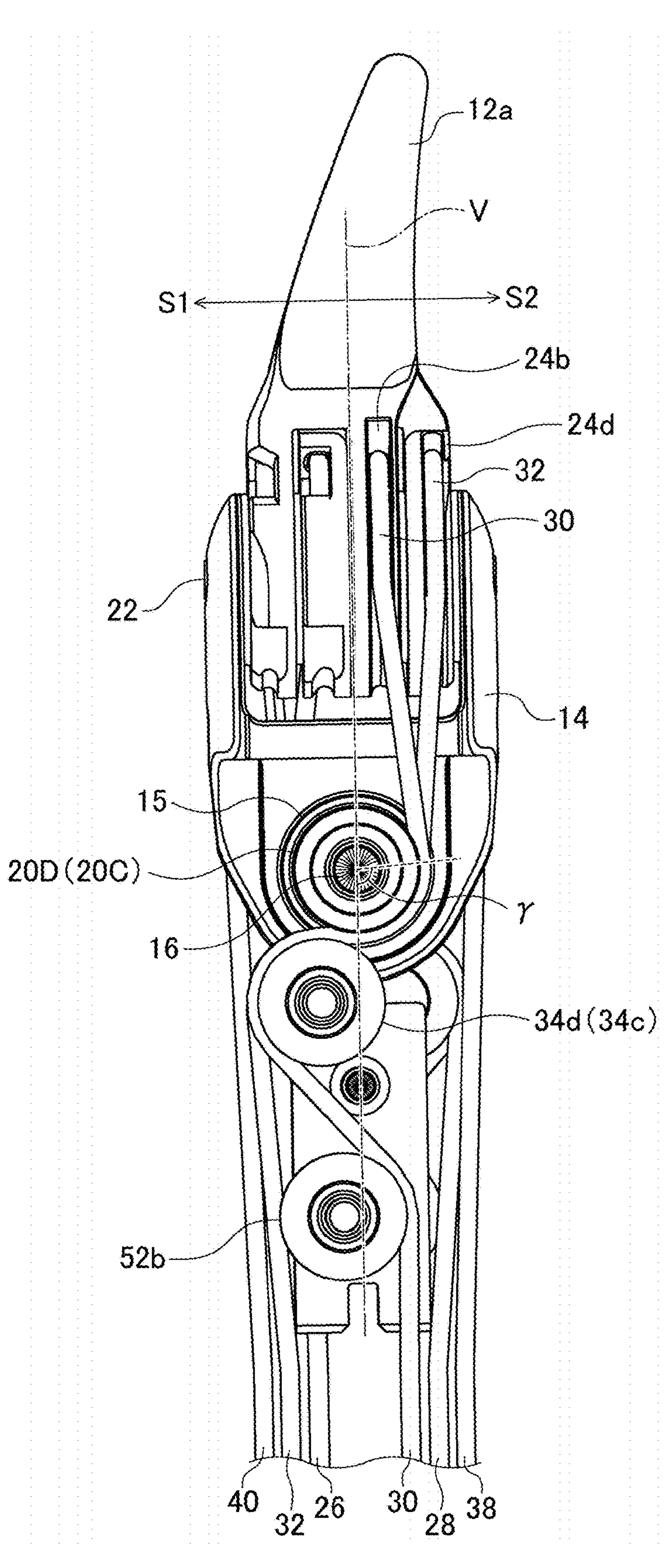
FIG. 15 is a schematic view of the forceps device illustrated in FIG. 4 omitting the base member, according to some embodiments.

FIG. 14 is a schematic view of the forceps device 10 illustrated in FIG. 3 omitting base member 18, according to some embodiments. FIG. 15 is a schematic view of the forceps device 10 illustrated in FIG. 4 omitting the base member, according to some embodiments.

As illustrated in FIGS. 10, 11, and 14, the wire 26 is passed over a first side S1 of the guide pulley 20A with respect to a vertical cross section V including the first rotating shaft 16 and being perpendicular to the second rotating shaft 22, and then fixed to the jaw pulley 24*c* located on the first side S1 with respect to the vertical cross section V. The wire 28 is passed over the first side S1 of the guide pulley 20B with respect to the vertical cross section V, and then fixed to the jaw pulley 24*a* located on the first side S1 with respect to the vertical cross section V.

In some embodiments, as illustrated in FIGS. 12, 13, and 15, the wire 30 is passed over the second side S2 of the guide pulley 20D with respect to the vertical cross section V, and then fixed to the jaw pulley 24*b* located on the second side with respect to the vertical cross section V. The wire 32 is passed over the second side S2 of the guide pulley 20C with respect to the vertical cross section V, and then fixed to the jaw pulley 24*d* located on the second side S2 with respect to the vertical cross section V. As a result, the four grasping-portion wires are fixed to the four grasping portion pulleys, respectively, without intersecting with each other.

In some embodiments, the forceps device 10 includes the guide pulley 34*a* on the upstream side of the guide pulley 20A (on the side opposite the grasping portions) and on the second side S2 with respect to the vertical cross section V, the guide pulley 34*b* on the upstream side of the guide pulley 20B and on the second side S2 with respect to the vertical cross section V, the guide pulley 34*c* on the upstream side of the guide pulley 20C and on the first side S1 with respect to the vertical cross section V, and the guide pulley 34*d* on the upstream side of the guide pulley 20D and on the first side S1 with respect to the vertical cross section V.

As a result, when the support 14 is bent in either direction about the first rotating shaft 16, one or more of the wires 26, 28, 30 and 32 come in contact with the associated one or more of the guide pulleys 20A to 20D, which stabilizes the controllability when the support 14 is turned. More specifically, when the support 14 is bent from the state illustrated in FIG. 14 toward the second side S2, the wires 26 and 28 come in contact with the guide pulleys 20A and 20B, respectively. In some embodiments, when the support 14 is bent from the state illustrated in FIG. 15 toward the first side S1, the wires 30 and 32 come in contact with the guide pulleys 20C and 20D, respectively. Thus, in either case, such a state in which none of the wires are in contact with the guide pulleys 20A to 20D (run over the guide pulleys 20A to 20D) is avoided. As a result, the controllability when the support 14 is bent about the first rotating shaft 16 is stabilized.

[Sealing of Base Member]

Because the grasping portions 12*a* and 12*b* of the forceps device 10 are operated inside the abdominal cavity of a patient, it is advantageous to devise a way to prevent gas around the grasping portions 12*a* and 12*b* from leaking out through the forceps device 10 so that the air pressure in the abdominal cavity, which is increased to be higher than the atmospheric pressure, does not lower. In some embodiments, sealing is therefore provided in a region including the base member 18.

Figure 16:
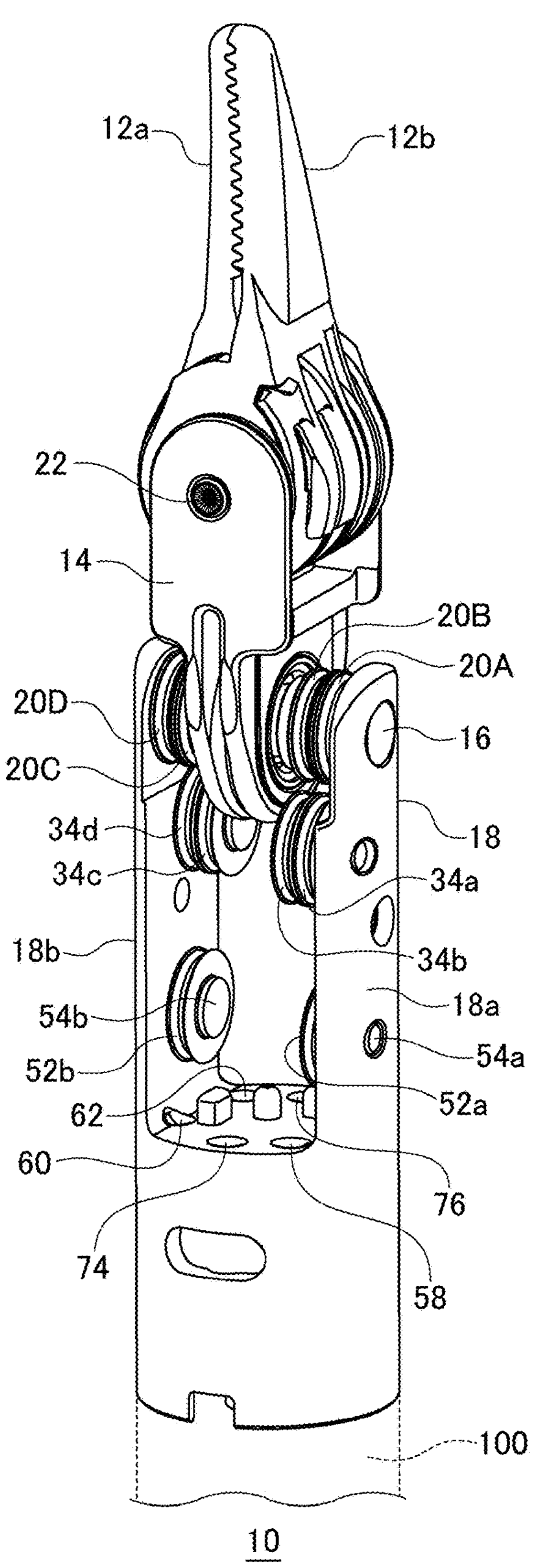
FIG. 16 is a schematic view of the forceps device illustrated in FIG. 1 omitting wires, according to some embodiments.

FIG. 16 is a schematic view of the forceps device illustrated in FIG. 1 omitting wires, according to some embodiments. As illustrated in FIG. 16, the forceps device 10 includes the pair of grasping portions 12*a* and 12*b*, the support 14 that holds the pair of grasping portions 12*a* and 12*b*, the first rotating shaft 16 that turnably supports the support 14, the base member 18 that holds the first rotating shaft 16, a plurality of wires 26, 28, 30 and 32 (not illustrated in FIG. 16; see FIG. 2) for transmitting driving forces to the pair of grasping portions 12*a* and 12*b* to move the grasping portions 12*a* and 12*b*, a guide pulley 52*a* for guiding the wire 26, a guide pulley 52*b* for guiding the wire 30, and support shafts 54*a* and 54*b* that rotatably support the guide pulleys 52*a* and 52*b*. The base member 18 is located between the grasping portions 12*a* and 12*b* and a shaft 100 of the forceps device 10.

Figure 17:
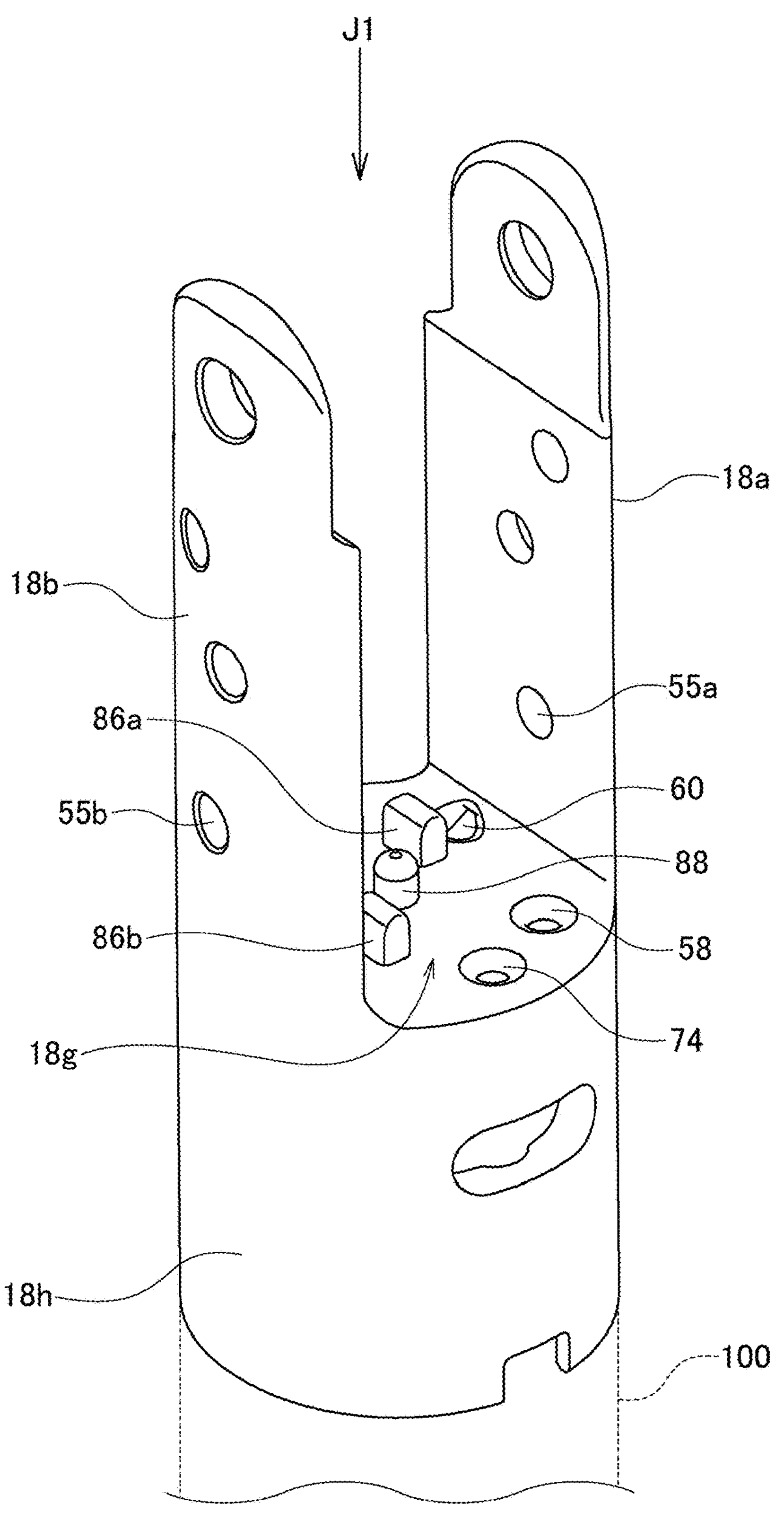
FIG. 17 is a perspective view of the base member according to an embodiment.
Figure 18:
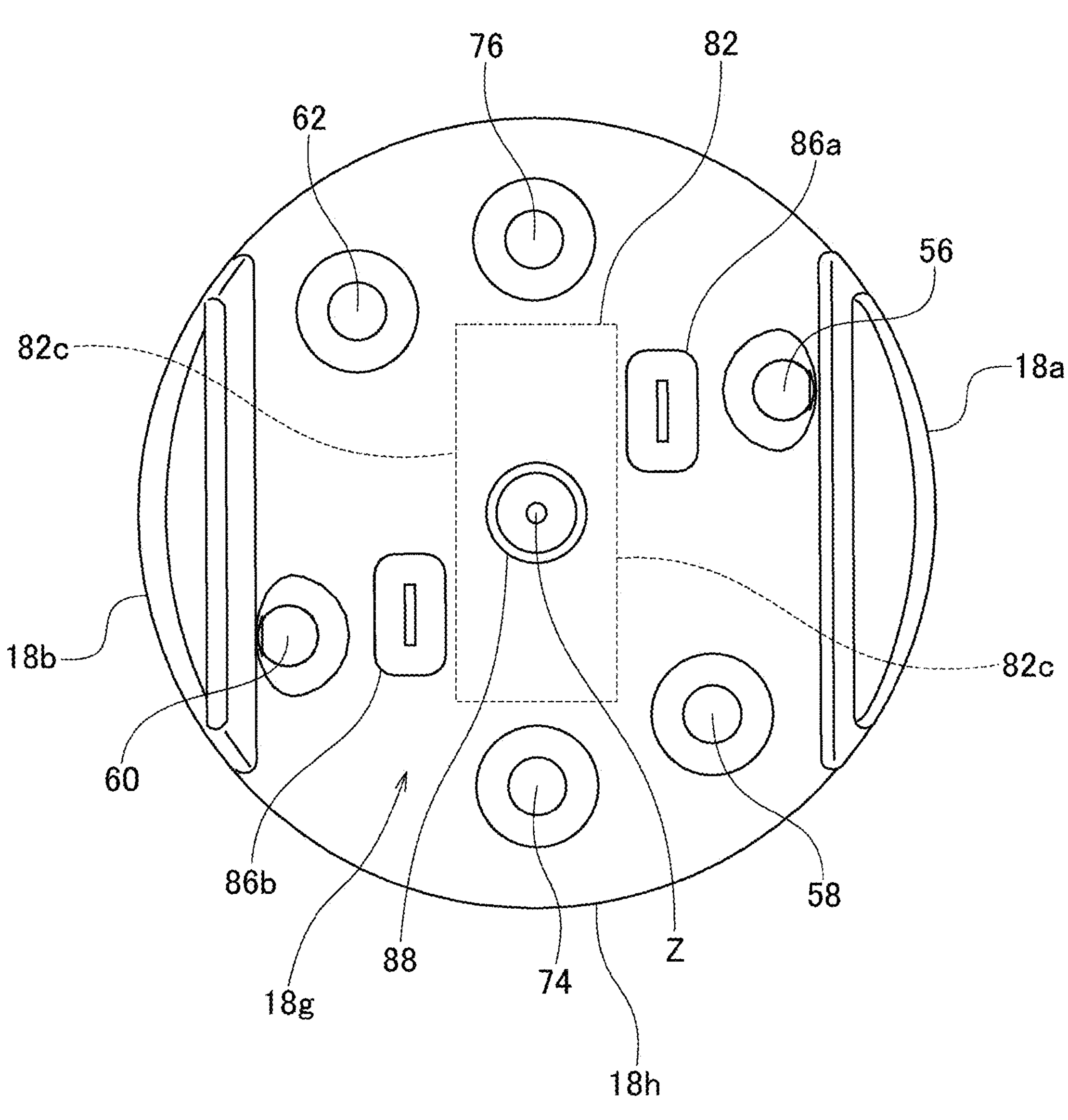
FIG. 18 is a top view of the base member illustrated in FIG. 17 as viewed in a direction J1.

FIG. 17 is a perspective view of the base member according to an embodiment. FIG. 18 is a top view of the base member illustrated in FIG. 17 as viewed in a direction J1.

The base member 18 includes a partition part 18*g* having a plurality of grasping-portion-wire holes 56, 58, 60 and 62 through which the wires 26, 28, 30 and 32, respectively, pass, and the pair of arms 18*a* and 18*b* which extend from an outer edge of the partition part 18*g* toward the grasping part (upward in FIG. 17) and to which the support shafts 54*a* and 54*b* are fixed. The arms 18*a* and 18*b* have fitting holes 55*a* and 55*b*, respectively, into which ends of the support shafts 54*a* and 54*b* that rotatably support the pair of guide pulleys 52*a* and 52*b* are fitted.

The partition part 18*g* is a partition formed between a cylindrical part 18*h* and the pair of arms 18*a* and 18*b*. The grasping-portion-wire holes 56 and 58 are a pair of grasping-portion-wire holes that are adjacent to each other at the closet distance, and the grasping-portion-wire holes 60 and 62 are a pair of grasping-portion-wire holes that are adjacent to each other at the closest distance.

As illustrated in FIG. 10, the wires 26 and 28 in a state being guided by the guide pulleys 34*a* and 34*b* are arranged together. Thus, for passing the wires 26 and 28 in this state through the partition part 18*g*, a large hole through which two wires can pass may be formed through the partition part 18*g* or two small holes through each of which one wire can pass may be formed through the partition part 18*g*. In the case of a large hole, the airtightness of sealing with sealing resin, which will be described later, may be lowered. In contrast, in the case of two adjacent small holes, the wall between the holes becomes thin, and the strength of an area of the base member 18 where the holes are formed may therefore be lowered.

Hence, in the forceps device 10, the wire 26 is guided by the guide pulley 52*a*, so that the wire 26 is separated from the wire 28. Similarly, the wire 30 is guided by the guide pulley 52*b*, so that the wire 30 is separated from the wire 32. In this manner, the grasping-portion-wire hole 56 through which the wire 26 passes and the grasping-portion-wire hole 58 through which the wire 28 passes can be separated from each other. Similarly, the grasping-portion-wire hole 60 through which the wire 30 passes and the grasping-portion-wire hole 62 through which the wire 32 passes can be separated from each other.

In some embodiments, the base member 18 includes an elastic sealing member (having a type A durometer hardness of 30 to 70) arranged on one side (on one side opposite the side in which the grasping portions 12*a* and 12*b* are located) with respect to the partition part 18*g*. The sealing member is a silicone resin film having a thickness of about 0.5 to 2 mm, for example.

The sealing member has a plurality of sealing holes at positions corresponding to those of the grasping-portion-wire holes 56, 58, 60 and 62. This configuration enables sealing with the sealing member, with the wires 26, 28, 30 and 32 passing through the partition part 18*g* of the base member 18. The wires have a diameter q of 0.4 to 0.5 mm, and the diameter of the grasping-portion-wire holes is preferably slightly larger than the wire diameter.

The sealing holes have a diameter that is smaller than the diameter of the grasping-portion-wire holes and smaller than the diameter (wire diameter q) of the grasping-portion wires. As a result, even when a gap is present between a grasping-portion-wire hole and a grasping-portion wire, the sealing hole and the grasping-portion wire are in close contact with each other, which reduces leakage of gas from the grasping part side to the outside of the forceps device 10 via the base member 18.

As illustrated in the drawings, the four grasping-portion-wire holes may be formed through the partition part 18*g* at certain distances from each other. Thus, the sealing holes formed at positions corresponding to those of the grasping-portion-wire holes are also separated from the adjacent sealing holes.

In some embodiments, the forceps device 10 includes the pair of wires 38 and 40 for turning the support 14 about the first rotating shaft 16 In some embodiments to the wires 26, 28, 30 and 32, which are grasping-portion wires. The partition part 18*g* of the base member 18 therefore has support-wire holes 74 and 76 through which the wires 38 and 40, respectively, pass. The support-wire holes 74 and 76 are formed at point-symmetric positions with respect to the center Z of the partition part 18*g* (the central axis of the cylindrical part 18*h*).

In some embodiments, the sealing member has a plurality of sealing holes formed at positions corresponding to those of the support-wire holes 74 and 76. This enables sealing with the sealing member, with the wires 38 and 40 passing through the partition part 18*g* of the base member 18. The diameter of the support-wire holes is preferably slightly larger than the wire diameter. In some embodiments, the arrangement of the pulleys of the forceps device 10 is devised so that a plurality of holes for wires formed in the partition part 18*g* of the base member 18 can be suitably separated from each other. This configuration reduces such a problem as unintended integration of holes for wires in forming the sealing member having a plurality of holes for wires.

[Turning Restricting Mechanism]

In the forceps device 10 illustrated in FIG. 2, in a state in which the driving force for turning the support 14 is transmitted via the wires 38 and 40, the grasping portions 12*a* and 12*b* are bent at an angle in a control range (±80° in the embodiment) that prevents part of the support 14 and the grasping-portion wires 26, 28, 30, and 32 from interfering with each other. In a state in which the forceps device 10 is detached from a power source or a main unit of a robot, however, the support 14 is freely turnable beyond the angles in the control range, and a partial region R of the support illustrated in FIG. 2 may therefore touch the grasping-portion wires 26, 28, 30, and 32.

Thus, the forceps device 10 includes a turning restricting mechanism for restricting turning of the support to prevent the turning support 14 from touching the grasping-portion wires 26, 28, 30, and 32. The turning restricting mechanism includes a stopper having a face with which part of the turning support comes into contact.

Figure 19:
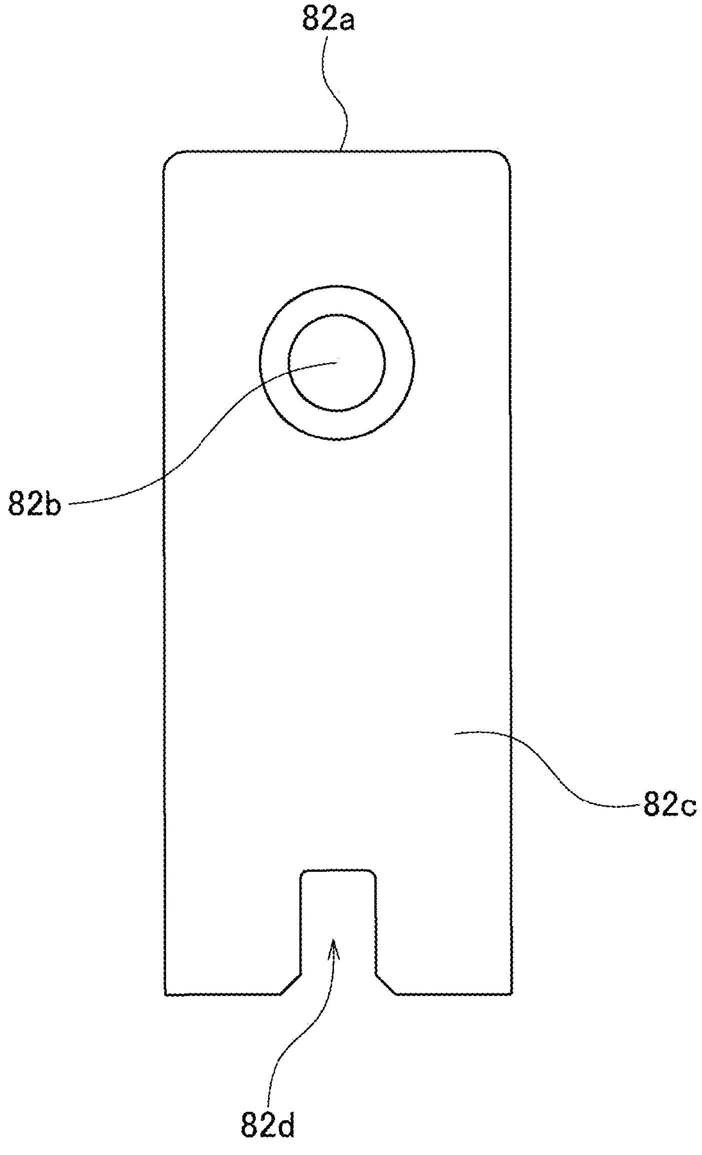
FIG. 19 is a front view of a stopper according to an embodiment.
Figure 20:
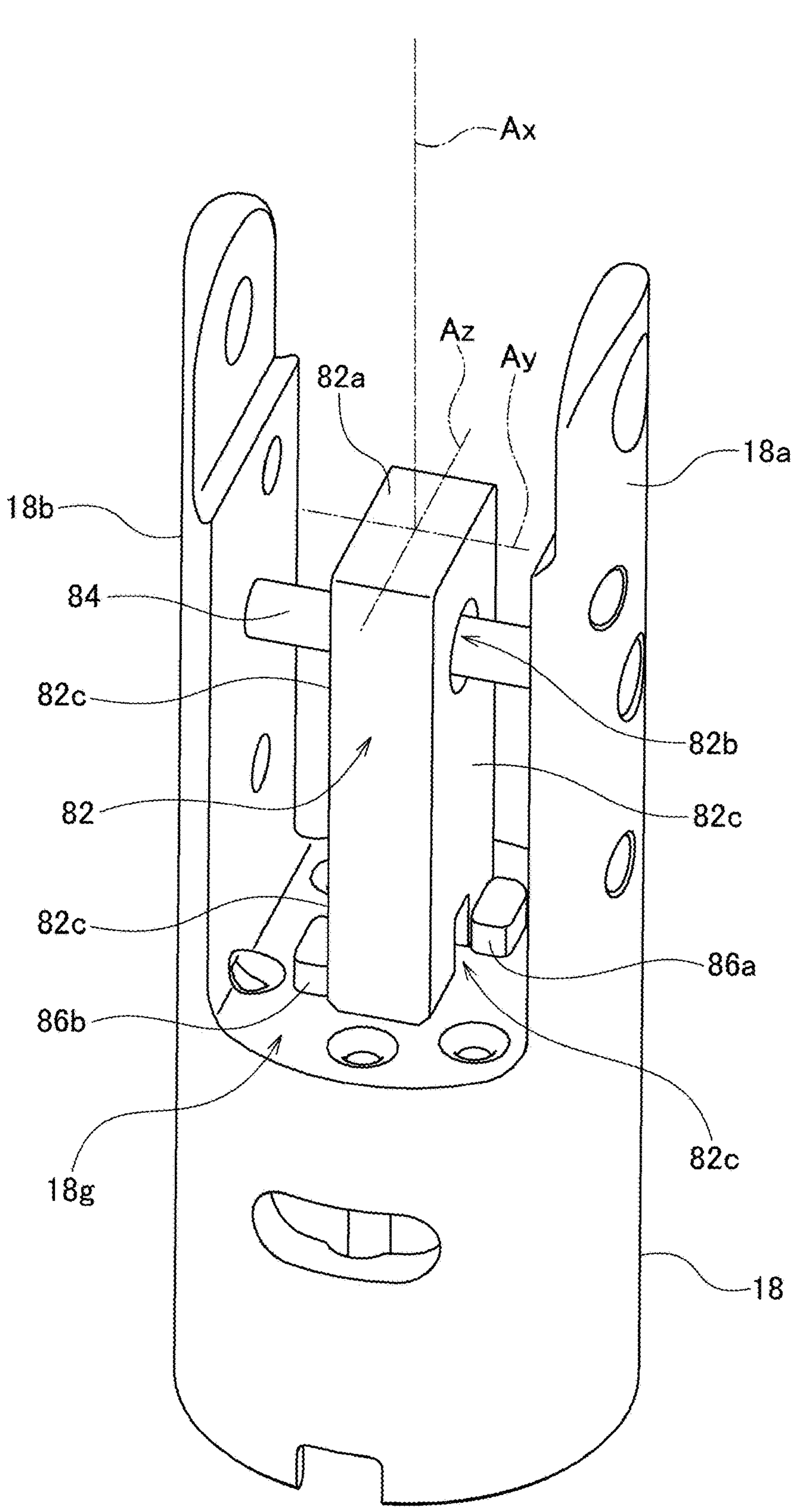
FIG. 20 is a drawing for explaining the stopper positioned in the base member, according to an embodiment.

FIG. 19 is a front view of the stopper according to an embodiment. FIG. 20 is a drawing for explaining the stopper positioned in the base member 18, according to an embodiment.

The stopper 82 is a block-like rectangular parallelepiped member having a flat face 82*a*, which faces the support 14, serving as the face with which the turning support comes into contact. When a contact face 14*b* of the support 14 comes into contact with the flat face 82*a* (see FIGS. 2 and 7 to 9), further turning of the support 14 is restricted. In this manner, the turning restricting mechanism is achieved with a simple part. Furthermore, because the support 14 is prevented from touching the grasping-portion wires 26, 28,

30, and 32, the durability of the grasping-portion wires is improved, and therefore the product life of the forceps device 10 is extended.

As described above, because the support 14 and the stopper 82 directly come in contact with each other, the turning restricting mechanism can more reliably prevent contact between the support and the grasping-portion wires.

In some embodiments, as illustrated in FIG. 7, the contact face 14*b* formed at an outer edge of the support 14 is a flat surface inclined with respect to the central axis Ax (the axis passing the center Z shown in FIG. 18) of the base member 18 at the neutral position (the state illustrated in FIG. 3, for example) at which the support 14 is not turned to the left or to the right. The support 14 is designed to come into contact with the stopper 82 when the turning angle from the neutral position becomes a contact angle β (α<β) beyond the angles α in the predetermined control range. This configuration and operation prevents the support 14 from turning at angles larger than the contact angle β while permitting turning at the angles α in the predetermined control range, which prevents hindrance to turning control of the support 14 by the stopper 82.

Note that, in some embodiments, the contact angle β may be 70° or larger. In some embodiments, the contact angle β may be larger than 90°. This configuration enables control of the turning of the support at least up to 70°. If the contact angle β is too large, however, the support 14 may touch the grasping-portion wires before the support 14 comes into contact with the stopper 82. In an embodiment, the contact angle β may be therefore smaller than a turning angle at which the support 14 touches a grasping-portion wire. Specifically, in an embodiment, the contact angle β may be smaller than 110°. In some embodiments, the contact angle β may be smaller than 100°.

Note that, if the contact angle β varies, the support 14 may unintentionally touch a grasping-portion wire. Positioning of the stopper 82 is therefore important. The stopper 82 is positioned relative to the base member 18. As a result, both the support 14 and the stopper 82 are at predetermined positions relative to the base member 18, which improves the accuracy of relative positions of the support 14 and the stopper 82.

Specific positioning in the embodiment will be explained. As illustrated in FIG. 19, a through-hole 82*b* is formed in a side face of the stopper 82. In some embodiments, as illustrated in FIG. 20, the pair of arms 18*a* and 18*b* of the base member 18 holds a positioning pin 84 that is inserted in and extending through the through-hole 82*b* of the stopper 82. Thus, the stopper 82 can be accurately positioned in the direction of the central axis Ax of the base member 18. Furthermore, because the pair of arms 18*a* and 18*b* holds the positioning pin 84, the strength of the arms is increased.

In some embodiments, the partition part 18*g* at the base part of the arms 18*a* and 18*b* of the base member 18 has a plurality of projections 86*a*, 86*b*, and 88 used for positioning of the stopper 82. The shapes and the arrangement of the projections 86*a* and 86*b* are set for positioning in a direction Ay intersecting the central axis Ax when the projections 86*a* and 86*b* come in contact with a pair of side faces 82*c*, which are opposite each other, of the stopper 82. In some embodiments, the shape and the arrangement of the projection 88 are set for positioning in a direction Az intersecting the central axis Ax and the direction Ay when the projection 88 is fitted into a groove 82*d* formed at a lower portion of the stopper 82. Thus, the stopper 82 can be accurately positioned in the directions Ay and Az intersecting the axial direction Ax of the base member 18.

In some embodiments, as illustrated in FIGS. 10 and 18, the stopper 82 is arranged in a region surrounded by a plurality of grasping-portion wires and support wires. Thus, the region surrounded by the plurality of wires is occupied by the stopper 82, which prevents foreign substances from staying inside the forceps device 10 (in a region surrounded by the wires) as compared with a case where no stopper is provided.

[Arrangement of Pulleys]

In the forceps device 10, the arrangement of the pulleys is devised so as to improve the durability of the wires while allowing some degree of wire winding angle. Specifically, as illustrated in FIG. 14, the guide pulleys 34*a* and 34*b* are shifted toward one side (toward S2) relative to a position immediately below the guide pulleys 20A and 20B when the first rotating shaft 16 is viewed in front in the axial direction in a state in which the leading ends of the grasping portions 12*a* and 12*b* point upward. Furthermore, the guide pulleys 34*a* and 34*b* are arranged so that the winding angle γ of the grasping-portion wires 26 and 28 around the guide pulleys 20A and 20B is 65° or larger at the neutral position at which the support 14 is not turned to the left or to the right.

This configuration enables comfortable operation control with the turning angle of the support 14, which holds the grasping portions 12*a* and 12*b*, being at least within a range of ±65°. Note that the winding angle γ may be 89° or larger. This configuration enables comfortable operation control with the turning angle of the support, which holds the grasping portions 12*a* and 12*b*, being at least within a range of ±89°.

The guide pulley 52*a* is located upstream of the guide pulleys 34*a* and 34*b*, and the grasping-portion wire 26 runs over the guide pulley 52*a*. The guide pulley 52*a* is shifted toward one side (toward S2) relative to immediately below the guide pulleys 20A and 20B and shifted toward the other side (toward S1) relative to immediately below the guide pulleys 34*a* and 34*b* when the first rotating shaft 16 is viewed in front in the axial direction in the state in which the leading ends of the grasping portions 12*a* and 12*b* point upward. This configuration increases the radius of curvature of an S-shaped curve of the grasping-portion wire 26 running over the guide pulley 34*a* and the guide pulley 52*a*. Furthermore, as a result of the increase in the radius of curvature of the S-shaped curve of the grasping-portion wire 26, bending stress generated in the grasping-portion wire 26 is lowered, and the durability of the grasping-portion wires relating to opening and closing movements of the grasping portions 12*a* and 12*b* is improved.

Similarly, as illustrated in FIG. 15, the guide pulleys 34*d* and 34*c* is shifted toward one side (toward S1) relative to immediately below the guide pulleys 20D and 20C when the first rotating shaft 16 is viewed in front in the axial direction in the state in which the leading ends of the grasping portions 12*a* and 12*b* point upward. In some embodiments, the guide pulleys 34*d* and 34*c* are arranged so that the winding angle γ of the grasping-portion wires 30 and 32 around the guide pulleys 20D and 20C is 65° or larger at the neutral position at which the support 14 is not turned to the left or to the right.

The guide pulley 52*b* is located upstream of the guide pulleys 34*d* and 34*c*, and the grasping-portion wire 30 runs over the guide pulley 52*b*. The guide pulley 52*b* is shifted toward one side (toward S1) relative to immediately below the guide pulleys 20D and 20C and shifted toward the other side (toward S2) relative to immediately below the guide pulleys 34*d* and 34*c* when the first rotating shaft 16 is viewed in front in the axial direction in the state in which the leading ends of the grasping portions 12*a* and 12*b* point upward. This configuration increases the radius of curvature of an S-shaped curve of the grasping-portion wire 30 running over the guide pulley 34*d* and the guide pulley 52*b*. Furthermore, as a result of the increase in the radius of curvature of the S-shaped curve of the grasping-portion wire 30, bending stress generated in the grasping-portion wire 30 is lowered, and the durability of the grasping-portion wires relating to opening and closing movements of the grasping portions 12*a* and 12*b* is improved.

Note that, as illustrated in FIG. 16, the guide pulleys 52*a* and 52*b* are located on respective sides of the inner wall of the base member 18. The guide pulleys 52*a* and 52*b* are also rotatably supported by different support shafts 54*a* and 54*b*, respectively, which are held by the base member 18. This configuration enables the guide pulley 52*a* and the guide pulleys 34*a* and 34*b* to be arranged on the same side (left side in FIG. 14) when the guide pulley 20A is viewed from the front. Similarly, the guide pulley 52*b* and the guide pulleys 34*c* and 34*d* can be arranged on the same side (left side in FIG. 15) when the guide pulley 20D is viewed from the front.

Note that the base member 18 is a cylindrical part having an outer diameter of 7 to 9 mm. Furthermore, the guide pulleys 20A to 20D have a diameter of 3.0 to 3.6 mm, the guide pulleys 34*a* to 34*d* have a diameter of 3.0 to 3.6 mm, and the guide pulleys 52*a* and 52*b* have a diameter of 3.0 to 3.6 mm. As a result, in a forceps device having a very small outer diameter, the radius of curvature of each S-shaped curve can be increased while appropriate winding angles are achieved.

While various embodiments have been described above with reference to the drawings, the various embodiments are not limited to the description above, and any combination or substitution of components as appropriate is included in the scope of the appended claims. In addition, modifications such as combinations, changes in the order of processes, and various changes in design may be made on an embodiment on the basis of knowledge of a person skilled in the art, and such modified embodiments may be within the scope of the appended claims.

What is claimed is:

1. A forceps device comprising:

a grasping part;

a support that holds the grasping part;

a first rotating shaft that turnably supports the support;

a base member that holds the first rotating shaft;

a plurality of grasping-portion wires that transmit driving forces to move the grasping part;

a plurality of first guide pulleys arranged coaxially with the first rotating shaft, the plurality of grasping-portion wires running over the plurality of first guide pulleys;

a plurality of second guide pulleys arranged upstream of the plurality of first guide pulleys on a side opposite the grasping part, the plurality of grasping-portion wires running over the plurality of second guide pulleys; and a plurality of third guide pulleys arranged upstream of the plurality of second guide pulleys on the side opposite the grasping part, the plurality of grasping-portion wires running over the plurality of third guide pulleys, wherein the plurality of second guide pulleys are:

shifted toward one side relative to a position immediately below the plurality of first guide pulleys when the first rotating shaft is viewed in front in an axial direction in a state in which a leading end of the grasping part points upward; and arranged so that a plurality of winding angles γ of the plurality of grasping-portion wires around the plurality of first guide pulleys are 65° or larger at a neutral position at which the support is not turned to left or right.

2. The forceps device according to claim 1, wherein each of the plurality of winding angles γ are 89° or larger.

3. The forceps device according to claim 2, wherein the plurality of third guide pulleys are:

shifted toward the one side relative to the position immediately below the plurality of first guide pulleys when the first rotating shaft is viewed in front in the axial direction in the state in which the leading end of the grasping part points upward; and shifted toward the other side relative to the position immediately below the plurality of second guide pulleys when the first rotating shaft is viewed in front in the axial direction in the state in which the leading end of the grasping part points upward.

4. The forceps device according to claim 3, wherein:

the base member is cylindrical and has an outer diameter of 7 mm to 9 mm, each of the plurality of first guide pulleys have a diameter of 3.0 mm to 3.6 mm, each of the plurality of second guide pulleys have a diameter of 3.0 mm to 3.6 mm, and each of the plurality of third guide pulleys have a diameter of 3.0 mm to 3.6 mm.

5. The forceps device according to claim 3, wherein:

the plurality of third guide pulleys comprise two third guide pulleys arranged on respective sides of an inner wall of the base member, and the two third guide pulleys are rotatably supported by different support shafts, respectively, held by the base member.

6. The forceps device according to claim 5, wherein:

the base member is cylindrical and has an outer diameter of 7 mm to 9 mm, each of the plurality of first guide pulleys have a diameter of 3.0 mm to 3.6 mm, each of the plurality of second guide pulleys have a diameter of 3.0 mm to 3.6 mm, and each of the plurality of third guide pulleys have a diameter of 3.0 mm to 3.6 mm.

7. The forceps device according to claim 1, wherein the plurality of third guide pulleys are:

shifted toward the one side relative to the position immediately below the plurality of first guide pulleys when the first rotating shaft is viewed in front in the axial direction in the state in which the leading end of the grasping part points upward; and shifted toward the other side relative to immediately below the plurality of second guide pulleys when the first rotating shaft is viewed in front in the axial direction in the state in which the leading end of the grasping part points upward.

8. The forceps device according to claim 7, wherein:

the base member is cylindrical and has an outer diameter of 7 mm to 9 mm, each of the plurality of first guide pulleys have a diameter of 3.0 mm to 3.6 mm, each of the plurality of second guide pulleys have a diameter of 3.0 mm to 3.6 mm, and each of the plurality of third guide pulleys have a diameter of 3.0 mm to 3.6 mm.

9. The forceps device according to claim 8, wherein:
the plurality of third guide pulleys comprise two third guide pulleys arranged on respective sides of an inner wall of the base member, and
the two third guide pulleys are rotatably supported by different support shafts, respectively, held by the base member.

10. The forceps device according to claim 7, wherein:
the plurality of third guide pulleys comprise two third guide pulleys arranged on respective sides of an inner wall of the base member, and
the two third guide pulleys are rotatably supported by different support shafts, respectively, held by the base member.

11. A forceps device comprising:
a plurality of grasping portions;
a support that holds the plurality of grasping portions;
a first rotating shaft that turnably supports the support;
a base member that holds the first rotating shaft;
a plurality of first wires that transmit driving forces to move the plurality of grasping portions;
a plurality of first guide pulleys arranged coaxially with the first rotating shaft, the plurality of first wires running over the plurality of first guide pulleys, respectively; and
a plurality of second guide pulleys arranged upstream of the plurality of first guide pulleys on a side opposite the plurality of grasping portions, the plurality of first wires running over the plurality of second guide pulleys, respectively; and
a plurality of third guide pulleys arranged upstream of the plurality of second guide pulleys on the side opposite the plurality of grasping portions, the plurality of first wires running over the plurality of third guide pulleys, respectively,
wherein the plurality of second guide pulleys are:
shifted toward one side relative to a position immediately below the plurality of first guide pulleys when the first rotating shaft is viewed in front in an axial direction in a state in which a leading end of the plurality of grasping portions points upward; and
arranged so that a plurality of winding angles γ of the plurality of first wires respective around the plurality of first guide pulleys are 65° or larger at a neutral position at which the support is not turned to left or right.

12. The forceps device according to claim 11, wherein each of the plurality of winding angles γ are 89° or larger.

13. The forceps device according to claim 12,
wherein the plurality of third guide pulleys are:
shifted toward the one side relative to the position immediately below the plurality of first guide pulleys when the first rotating shaft is viewed in front in the axial direction in the state in which the leading end of the plurality of grasping portions points upward; and
shifted toward the other side relative to the position immediately below the plurality of second guide pulleys when the first rotating shaft is viewed in front in the axial direction in the state in which the leading end of the plurality of grasping portions points upward.

14. The forceps device according to claim 13, wherein:
the base member is cylindrical and has an outer diameter of 7 mm to 9 mm,
each of the plurality of first guide pulleys have a diameter of 3.0 mm to 3.6 mm,
each of the plurality of second guide pulleys have a diameter of 3.0 mm to 3.6 mm, and
each of the plurality of third guide pulleys have a diameter of 3.0 mm to 3.6 mm.

15. The forceps device according to claim 13, wherein:
the plurality of third guide pulleys comprise two third guide pulleys arranged on respective sides of an inner wall of the base member, and
the two third guide pulleys are rotatably supported by different support shafts, respectively, held by the base member.

16. The forceps device according to claim 15, wherein:
the base member is cylindrical and has an outer diameter of 7 mm to 9 mm,
each of the plurality of first guide pulleys have a diameter of 3.0 mm to 3.6 mm,
each of the plurality of second guide pulleys have a diameter of 3.0 mm to 3.6 mm, and
each of the plurality of third guide pulleys have a diameter of 3.0 mm to 3.6 mm.

17. The forceps device according to claim 11,
wherein the plurality of third guide pulleys are:
shifted toward the one side relative to the position immediately below the plurality of first guide pulleys when the first rotating shaft is viewed in front in the axial direction in the state in which the leading end of the plurality of grasping portions points upward; and
shifted toward the other side relative to immediately below the plurality of second guide pulleys when the first rotating shaft is viewed in front in the axial direction in the state in which the leading end of the plurality of grasping portions points upward.

18. The forceps device according to claim 17, wherein:
the base member is cylindrical and has an outer diameter of 7 mm to 9 mm,
each of the plurality of first guide pulleys have a diameter of 3.0 mm to 3.6 mm,
each of the plurality of second guide pulleys have a diameter of 3.0 mm to 3.6 mm, and
each of the plurality of third guide pulleys have a diameter of 3.0 mm to 3.6 mm.

19. The forceps device according to claim 18, wherein:
the plurality of third guide pulleys comprise two third guide pulleys arranged on respective sides of an inner wall of the base member, and
the two third guide pulleys are rotatably supported by different support shafts, respectively, held by the base member.

20. The forceps device according to claim 17, wherein:
the plurality of third guide pulleys comprise two third guide pulleys arranged on respective sides of an inner wall of the base member, and
the two third guide pulleys are rotatably supported by different support shafts, respectively, held by the base member.

* * * * *